United States Patent
Spiro et al.

(10) Patent No.: US 12,357,341 B2
(45) Date of Patent: Jul. 15, 2025

(54) CUTTING INSTRUMENT WITH IMPROVED SURFACE TOPOGRAPHY

(71) Applicant: Entrepix Medical, LLC, Phoenix, AZ (US)

(72) Inventors: Clifford Spiro, Phoenix, AZ (US); Timothy Tobin, Phoenix, AZ (US); Eric Coats, Phoenix, AZ (US); William Fender, Phoenix, AZ (US)

(73) Assignee: PLANATOME, LLC, Phoenix, AZ (US)

( * ) Notice: Subject to any disclaimer, the term of this patent is extended or adjusted under 35 U.S.C. 154(b) by 720 days.

(21) Appl. No.: 17/491,512

(22) Filed: Sep. 30, 2021

(65) Prior Publication Data

US 2022/0096114 A1 Mar. 31, 2022

Related U.S. Application Data

(60) Provisional application No. 63/085,952, filed on Sep. 30, 2020.

(51) Int. Cl.
*A61B 17/3211* (2006.01)
*A61B 17/00* (2006.01)
*B24B 37/04* (2012.01)

(52) U.S. Cl.
CPC ........ *A61B 17/3211* (2013.01); *B24B 37/042* (2013.01); *A61B 2017/00526* (2013.01); *A61B 2017/00849* (2013.01)

(58) Field of Classification Search
CPC ....................................... A61B 17/3211–3217
See application file for complete search history.

(56) References Cited

U.S. PATENT DOCUMENTS

| | | | | |
|---|---|---|---|---|
| 4,926,309 A | * | 5/1990 | Wu | G05B 19/4163 706/904 |
| 4,980,021 A | * | 12/1990 | Kitamura | C23C 16/277 216/81 |
| 5,230,833 A | * | 7/1993 | Romberger | C09K 3/1463 516/928 |
| 6,379,858 B1 | * | 4/2002 | Perry | G03G 5/10 430/127 |
| 7,037,175 B1 | * | 5/2006 | Spiro | B24B 3/36 76/82 |
| 11,224,921 B2 | * | 1/2022 | Sasaki | B23D 77/00 |
| 11,592,770 B2 | * | 2/2023 | Shimada | G03G 15/2064 |

(Continued)

FOREIGN PATENT DOCUMENTS

| | | |
|---|---|---|
| CN | 106965044 | 7/2020 |
| JP | 2011217949 | 11/2011 |
| WO | 2006044466 | 4/2006 |

OTHER PUBLICATIONS

International Search Report and Written Opinon for corresponding PCT Application No. PCT/US21/053045 Jan. 20, 2022.

(Continued)

*Primary Examiner* — Adam J Eiseman
*Assistant Examiner* — Richard D Crosby, Jr.
(74) *Attorney, Agent, or Firm* — BRYAN CAVE LEIGHTON PAISNER LLP

(57) ABSTRACT

Various embodiments for an improved cutting instrument defining one or more angularly-oriented cutting fasciae having uniform cutting surfaces with reduced surface topography are disclosed.

20 Claims, 14 Drawing Sheets

(56) References Cited

U.S. PATENT DOCUMENTS

| | | | | |
|---|---|---|---|---|
| 2002/0106978 | A1* | 8/2002 | Michaud | B24B 33/00 451/48 |
| 2003/0148716 | A1* | 8/2003 | Lyons, III | B24D 15/066 451/45 |
| 2006/0084367 | A1* | 4/2006 | Spiro | B24B 3/36 451/45 |
| 2009/0113726 | A1* | 5/2009 | Ducros | C23C 14/0688 204/192.16 |
| 2009/0208250 | A1* | 8/2009 | Mitsumori | G03G 5/0564 430/65 |
| 2010/0023041 | A1 | 1/2010 | Satake | |
| 2010/0087845 | A1* | 4/2010 | Spiro | A61B 17/3211 606/167 |
| 2011/0232108 | A1* | 9/2011 | Ochiai | C23C 30/005 30/345 |
| 2012/0222315 | A1* | 9/2012 | Buchtmann | C23C 14/3414 30/244 |
| 2015/0158268 | A1* | 6/2015 | Koike | B32B 3/30 156/247 |
| 2016/0068449 | A1* | 3/2016 | Tsukihara | C04B 35/58014 407/119 |
| 2016/0115624 | A1* | 4/2016 | Pels | C30B 33/00 83/13 |
| 2018/0292768 | A1* | 10/2018 | Imase | G03G 15/0818 |
| 2020/0230705 | A1* | 7/2020 | Sasaki | B23D 77/00 |
| 2021/0162718 | A1* | 6/2021 | Huang | B32B 17/10605 |
| 2022/0299920 | A1* | 9/2022 | Shimada | G03G 15/2025 |

OTHER PUBLICATIONS

Chen, H., et al., "Highly Polished Scalpel Blades Reduce Incisional Wound Scar Variability in Duroc Pigs," Open Access Journal of Surgery, vol. 12, Issue 2, ISSN: 2476-1346, 10 pgs, Oct. 12, 2020.
Prescher, H., et al., "Scalpel Edge Roughness Affects Post-Transection Peripheral Nerve Regeneration," Surgery Open Science 4 (2021) 1-6, Nov. 18, 2020.

* cited by examiner

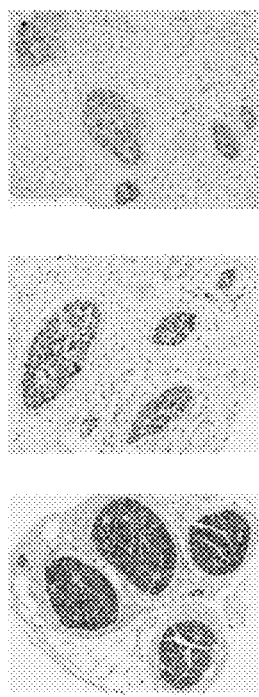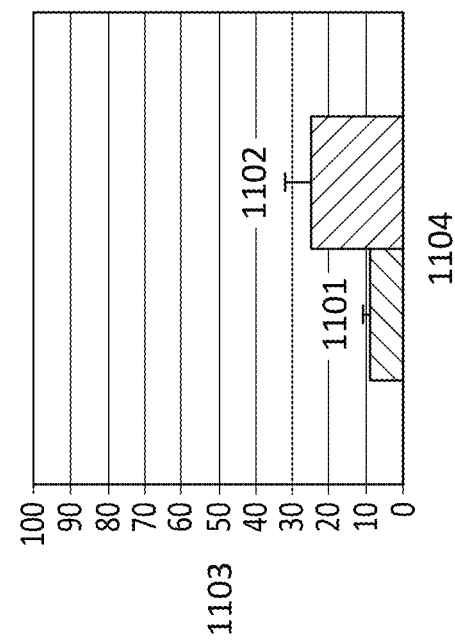

CUTTING INSTRUMENT WITH IMPROVED SURFACE TOPOGRAPHY

CROSS-REFERENCE TO RELATED APPLICATIONS

This application claims the benefit of U.S. Provisional 63/085,952, filed Sep. 30, 2020, which is herein incorporated by this reference in its entirety.

TECHNICAL FIELD

The present disclosure generally relates to cutting instruments, such as scalpel blades, keratomes, scissors, osteotome, endocutters and other medical devices whose purpose is to cut (e.g., make incisions in and resections of living tissue), as well as non-medical cutting instruments. More specifically, this disclosure is related to improving said cutting instruments by creating a nano-precise, highly uniform, ultra-smooth surface topography on cutting surfaces.

BACKGROUND

Currently, cutting instruments (e.g., a scalpel) often incorporate a handle and a blade either as a single unit or one with a reusable handle and replaceable blade. Such cutting instruments typically come in various shapes and sizes depending on their purpose, which, in the case of scalpels, are each identified using a numbering system. For example, #15 and #10 scalpel blades have a curved cutting edge and can be used for general tissue incisions. As another example, #11 scalpel blades can have a linear cutting edge and a sharp point that can be used for puncturing type incisions. Many cutting instruments are manufactured from stainless steel or carbon steel, but other materials of suitable hardness can also be used (e.g., diamond, sapphire, ceramics, etc. . . . ).

One current method for blade manufacturing is to stamp a near-net shape blade blank from a metal sheet, followed by double-edge bevel grinding using two diamond-embedded disks or grinding wheels, where each disk or wheel is tilted at an angle of approximately 10-20 degrees. The purpose of the diamonds is to act as a grinding medium that rapidly ploughs the metal surfaces into two angularly-oriented faces, referred to collectively as the "fasciae," or individually as a "fascia," that then meet to create an edge. This method can cause a number of problems. For example, diamonds embedded in the grinding disk or wheel are discrete, individual crystals of varying sizes and shapes and are non-uniformly spaced on the grinding wheel. This factor alone can result in a non-uniform grind. In addition, the diamonds often fracture during the grinding operation, thereby causing the grind to become even less uniform. Non-uniform diamond ploughing can often leave quasi-parallel tracks of varying depths, profiles, and spacing along the cutting fasciae of the scalpel, thereby resulting in ragged, rough, serrated cutting surfaces on the cutting instrument. When the two fasciae come together to form a leading edge, the uneven grind marks are projected onto the leading edge, thereby resulting in the leading edge being jagged, rough, and quasi-serrated. In surgical cutting instruments, conventionally produced cutting instruments act contrary to Halsted's principles of surgical technique, which emphasizes, among other things, gentle tissue handling for optimal clinical outcomes. These ragged edges and serrations present along the cutting fasciae and associated leading edge of a standard surgical blade can cause multiple problems, particularly when they contact and incise tissue, including (but not limited to):

(i) lack of precision for exact incision placement;
(ii) micro-tearing of tissue creating excess and undue trauma and/or bleeding, thereby elongating the healing process;
(iii) defect sites for tissue caking and serration fold-over resulting in the need to replace cutting instruments during surgical procedures, often multiple times;
(iv) weakened material sites more prone to fracture when contacting bone or other hard structures; and/or
(v) high variability of cutting performance from one cutting instrument to the next, even within the same manufacturing lot of cutting instruments.

It is with these observations in mind, among others, that various aspects of the present disclosure were conceived and developed.

BRIEF DESCRIPTION OF THE DRAWINGS

FIG. 11A shows an exemplary a graphical representation comparing performance of a standard blade with a cutting instrument having improved surface topography, as described herein;

FIGS. 11B-11D show exemplary cell micrographs of *Cavia porcellus* axons;

Corresponding reference characters indicate corresponding elements among the view of the drawings. The headings used in the figures do not limit the scope of the claims.

Figure 1:
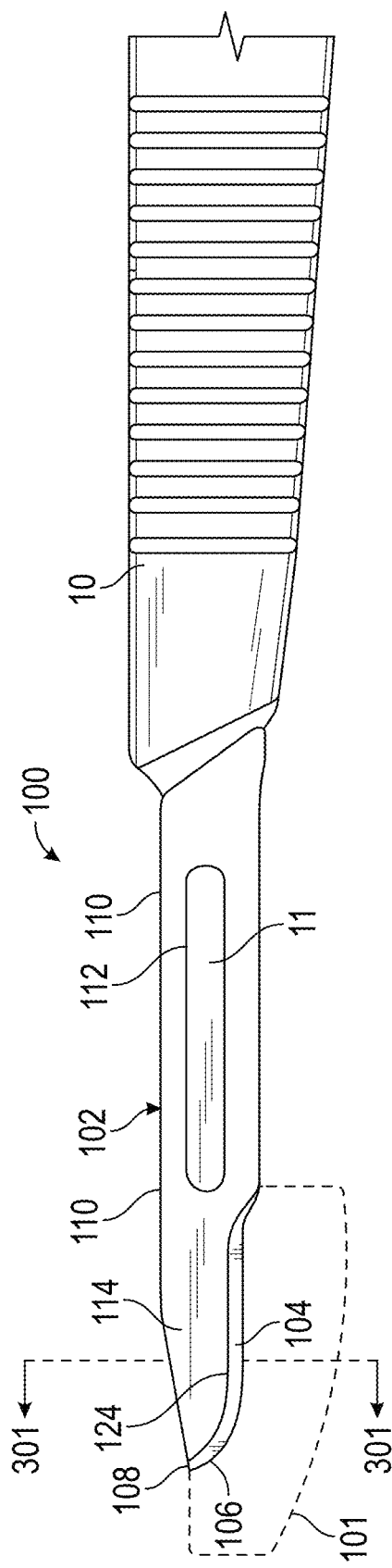
FIG. 1 shows an exemplary side view of a cutting instrument having a blade body coupled to a handle.

For simplicity and clarity of illustration, the drawing figures illustrate the general manner of construction, and descriptions and details of well-known features and techniques may be omitted to avoid unnecessarily obscuring the present disclosure. Additionally, elements in the drawing figures are not necessarily drawn to scale. For example, the dimensions of some of the elements in the figures may be exaggerated relative to other elements to help improve understanding of embodiments of the present disclosure. The same reference numerals in different figures denote the same elements.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Furthermore, the terms "include," and "have," and any variations thereof, are intended to cover a non-exclusive inclusion, such that a process, method, system, article, device, or apparatus that comprises a list of elements is not necessarily limited to those elements, but may include other elements not expressly listed or inherent to such process, method, system, article, device, or apparatus.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments of the apparatus, methods, and/or articles of manufacture described herein are, for example, capable of operation in other orientations than those illustrated or otherwise described herein.

The terms "couple," "coupled," "couples," "coupling," and the like should be broadly understood and refer to connecting two or more elements mechanically and/or otherwise. Two or more electrical elements may be electrically coupled together, but not be mechanically or otherwise coupled together. Coupling may be for any length of time, e.g., permanent or semi-permanent or only for an instant. "Electrical coupling" and the like should be broadly understood and include electrical coupling of all types. The absence of the word "removably," "removable," and the like near the word "coupled," and the like does not mean that the coupling, etc. in question is or is not removable.

As defined herein, two or more elements are "integral" if they are comprised of the same piece of material. As defined herein, two or more elements are "non-integral" if each is comprised of a different piece of material.

As used herein, a "working portion" of a cutting wedge, can comprise any portion, portions, or all of the areas of a cutting wedge intended to incise or actually make contact with the material to be incised, such as human tissue.

DETAILED DESCRIPTION

Various embodiments of a cutting instrument having a blade body with a nano-precise, highly uniform, ultra-smooth cutting fasciae are disclosed herein. In one aspect, the blade body has been manufactured to define one or more angularly-oriented cutting fasciae having minimal surface roughness, as measured by a plurality of areal method parameters to produce a cutting instrument having improved nano-precise uniform surface topography.

In various embodiments, a cutting instrument is disclosed. The cutting instrument can comprise a blade body having two opposing faces and a cutting wedge that can comprise: a leading edge; and one or more cutting fasciae extending from at least one of the two opposing faces and defining at least a portion of the leading edge, wherein the one or more cutting fasciae can have a surface roughness comprising a measured arithmetic mean height ($S_a$) of 150 nm or less with a standard deviation of 30 nm or less across a measurement area of 129 μm×129 μm on at least a portion of the one or more cutting fasciae. In the sane or different embodiments, the surface roughness also can comprise one or more of: (1) a measured maximum height ($S_z$) of 1.5 μm or less with a standard deviation of 0.4 μm or less within the measurement area of 129 μm×129 μm on the at least the portion of the one or more cutting fasciae; or (2) a measured arithmetic mean peak curvature ($S_{pc}$) of 150 mm$^{-1}$ or less with a standard deviation of 30 mm$^{-1}$ or less within the measurement area of 129 μm×129 μm on the at least the portion of the one or more cutting fasciae.

In many embodiments, a method of manufacturing a cutting instrument is disclosed. The method can comprise: providing a blade body having two opposing faces and a cutting wedge that can comprise: a leading edge; and one or more cutting fasciae extending from at least one of the two opposing faces and defining at least a portion of the leading edge, wherein the one or more cutting fasciae can have a surface roughness comprising a measured arithmetic mean height ($S_a$) of 150 nm or less with a standard deviation of 30 nm or less across a measurement area of 129 μm×129 μm on at least a portion of the one or more cutting fasciae. In the sane or different embodiments, the surface roughness also can comprise one or more of: (1) a measured maximum height ($S_z$) of 1.5 μm or less with a standard deviation of 0.4 μm or less within the measurement area of 129 μm×129 μm on the at least the portion of the one or more cutting fasciae; or (2) a measured arithmetic mean peak curvature ($S_{pc}$) of 150 mm$^{-1}$ or less with a standard deviation of 30 mm$^{-1}$ or less within the measurement area of 129 μm×129 μm on the at least the portion of the one or more cutting fasciae.

In various embodiments, a cutting instrument is disclosed. The cutting instrument can comprise a blade body having two opposing faces and a cutting wedge that can comprise: a leading edge; and one or more cutting fasciae extending from at least one of the two opposing faces and defining at least a portion of the leading edge, wherein the one or more cutting fasciae can have a surface roughness comprising a measured dale void volume ($V_{vv}$) of 0.02 μm$^3$/μm$^2$ or less with a standard deviation of 0.005 μm$^3$/μm$^2$ or less across a measurement area of 129 μm×129 μm on the at least a portion of the one or more cutting fasciae. In the sane or different embodiments, the surface roughness also can comprise one or more of: (1) a measured maximum height ($S_z$) of 1.5 μm or less with a standard deviation of 0.4 μm or less within the measurement area of 129 μm×129 μm on the at least the portion of the one or more cutting fasciae; or (2) a measured arithmetic mean peak curvature ($S_{pc}$) of 150 mm$^{-1}$ or less with a standard deviation of 30 mm$^{-1}$ or less within the measurement area of 129 μm×129 μm on the at least the portion of the one or more cutting fasciae.

In many embodiments, a method of manufacturing a cutting instrument is disclosed. The method can comprise: providing a blade body having two opposing faces and a cutting wedge comprising: a leading edge; and one or more cutting fasciae extending from at least one of the two opposing faces and defining at least a portion of the leading edge, wherein the one or more cutting fasciae have a surface roughness comprising a measured dale void volume ($V_{vv}$) of 0.02 $\mu m^3/\mu m^2$ or less with a standard deviation of 0.005 $\mu m^3/\mu m^2$ or less across a measurement area of 129 $\mu m \times 129$ $\mu m$ on the at least a portion of the one or more cutting fasciae. In the sane or different embodiments, the surface roughness also can comprise one or more of: (1) a measured maximum height ($S_z$) of 1.5 $\mu m$ or less with a standard deviation of 0.4 $\mu m$ or less within the measurement area of 129 $\mu m \times 129$ $\mu m$ on the at least the portion of the one or more cutting fasciae; or (2) a measured arithmetic mean peak curvature ($S_{pc}$) of 150 $mm^{-1}$ or less with a standard deviation of 30 $mm^{-1}$ or less within the measurement area of 129 $\mu m \times 129$ $\mu m$ on the at least the portion of the one or more cutting fasciae.

In various embodiments, a cutting instrument is disclosed. The cutting instrument can comprise a blade body having two opposing faces and a cutting wedge that can comprise: a leading edge; and one or more cutting fasciae extending from at least one of the two opposing faces and defining at least a portion of the leading edge, wherein the one or more cutting fasciae can have a surface roughness comprising: (1) a measured arithmetic mean height ($S_a$) of 150 nm or less with a standard deviation of 30 nm or less across a measurement area of 129 $\mu m \times 129$ $\mu m$ on at least a portion of the one or more cutting fasciae or (2) a measured dale void volume ($V_{vv}$) of 0.02 $\mu m^3/\mu m^2$ or less with a standard deviation of 0.005 $\mu m^3/\mu m^2$ or less across the measurement area of 129 $\mu m \times 129$ $\mu m$ on the at least the portion of the one or more cutting fasciae. In the sane or different embodiments, the surface roughness also can comprise one or more of: (1) a measured maximum height ($S_z$) of 1.5 $\mu m$ or less with a standard deviation of 0.4 $\mu m$ or less within the measurement area of 129 $\mu m \times 129$ $\mu m$ on the at least the portion of the one or more cutting fasciae; or (2) a measured arithmetic mean peak curvature ($S_{pc}$) of 150 $mm^{-1}$ or less with a standard deviation of 30 $mm^{-1}$ or less within the measurement area of 129 $\mu m \times 129$ $\mu m$ on the at least the portion of the one or more cutting fasciae.

In many embodiments, a method of manufacturing a cutting instrument is disclosed. The method can comprise: providing a blade body having two opposing faces and a cutting wedge that can comprise: a leading edge; and one or more cutting fasciae extending from at least one of the two opposing faces and defining at least a portion of the leading edge, wherein the one or more cutting fasciae can have a surface roughness comprising: (1) a measured arithmetic mean height ($S_a$) of 150 nm or less with a standard deviation of 30 nm or less across a measurement area of 129 $\mu m \times 129$ $\mu m$ on at least a portion of the one or more cutting fasciae or (2) a measured dale void volume ($V_{vv}$) of 0.02 $\mu m^3/\mu m^2$ or less with a standard deviation of 0.005 $\mu m^3/\mu m^2$ or less across the measurement area of 129 $\mu m \times 129$ $\mu m$ on the at least the portion of the one or more cutting fasciae. In the sane or different embodiments, the surface roughness also can comprise one or more of: (1) a measured maximum height ($S_z$) of 1.5 $\mu m$ or less with a standard deviation of 0.4 $\mu m$ or less within the measurement area of 129 $\mu m \times 129$ $\mu m$ on the at least the portion of the one or more cutting fasciae; or (2) a measured arithmetic mean peak curvature ($S_{pc}$) of 150 $mm^{-1}$ or less with a standard deviation of 30 $mm^{-1}$ or less within the measurement area of 129 $\mu m \times 129$ $\mu m$ on the at least the portion of the one or more cutting fasciae.

In various embodiments, a method of improving surface topography of a cutting instrument is disclosed. The method can comprise: applying a polishing apparatus to at least one side of a cutting wedge of the cutting instrument; actuating the polishing apparatus on the at least one side of the cutting wedge of the cutting instrument using a first pressure; and, as the polishing apparatus approaches a leading edge of the cutting wedge of the cutting instrument, actuating the polishing apparatus on the at least one side of the cutting wedge of the cutting instrument using a second pressure that is less than the first pressure. In some embodiments, the cutting wedge has a surface roughness can further comprise one or more of: (1) a measured arithmetic mean height ($S_a$) of 150 nm or less with a standard deviation of 30 nm or less across a measurement area of 129 $\mu m \times 129$ $\mu m$ on at least a portion of the one or more cutting fasciae or (2) a measured dale void volume ($V_{vv}$) of 0.02 $\mu m^3/\mu m^2$ or less with a standard deviation of 0.005 $\mu m^3/\mu m^2$ or less across the measurement area of 129 $\mu m \times 129$ $\mu m$ on the at least the portion of the one or more cutting fasciae; (3) a measured maximum height ($S_z$) of 1.5 $\mu m$ or less with a standard deviation of 0.4 $\mu m$ or less within the measurement area of 129 $\mu m \times 129$ $\mu m$ on the at least the portion of the one or more cutting fasciae; or (4) a measured arithmetic mean peak curvature ($S_{pc}$) of 150 $mm^{-1}$ or less with a standard deviation of 30 $mm^{-1}$ or less within the measurement area of 129$\times$129 $\mu m$ on the at least the portion of the one or more cutting fasciae.

Generally speaking, embodiments of a cutting instrument with improved surface topography and methods of making the same are disclosed herein. While some embodiments of the cutting instrument with improved surface topography described herein are for surgical applications, a person having ordinary skill in the art will understand that the instruments and methods described herein are not limited to surgical applications. For example, instruments and methods described herein can be used in teeth cleaning and other dentistry applications, carpentry applications, food processing applications, lumber processing, paper production, horticulture, etc. Further, a person having ordinary skill in the art will understand that instruments and methods described here can take many forms. For example, a cutting instrument can comprise die cutting tools, stamps, reamers, milling tools, end mills, broaches, taps, thread cutting die, cleavers, slitters, saw blades, etc.

Figure 2:
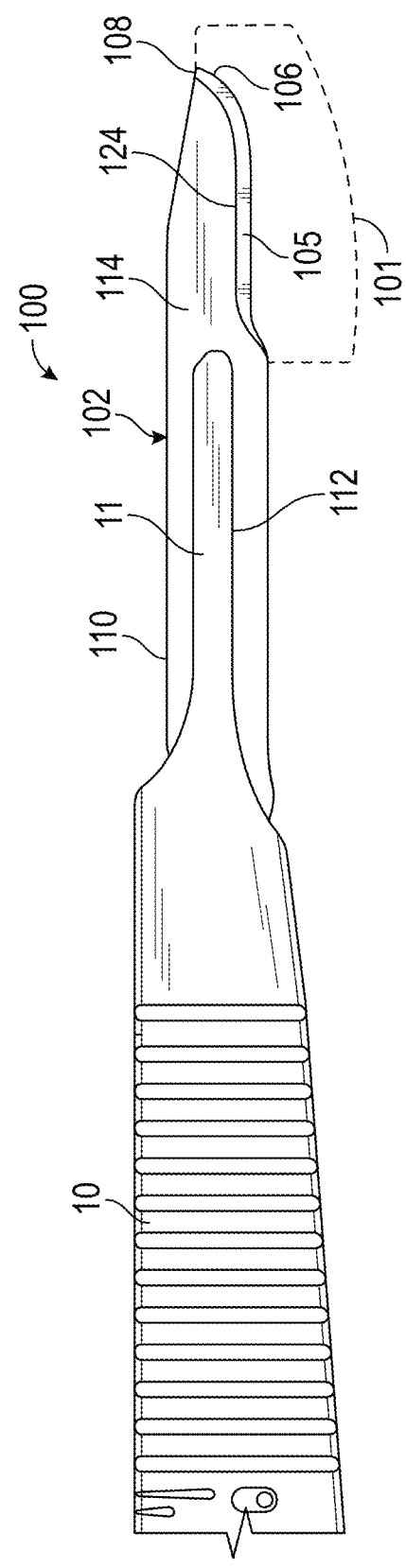
FIG. 2 shows an exemplary opposite side view of the cutting instrument of FIG. 1.

Referring now to FIGS. 1 and 2, an exemplary embodiment of a cutting instrument 100 is shown. In some embodiments, cutting instrument 100 can include a blade body 102, a slot 112, opposing faces 114 and 115, and/or a spine 110. In various embodiments, a blade body can comprise a shape that facilitates transfer of force through a cutting instrument. In various embodiments, a blade body's shape can vary depending on an intended use for a cutting instrument. For example, blade body 102 is shaped similar to a #15 scalpel blade, which can be used for making tissue incisions using a slicing motion that moves approximately parallel to the skin. As another example, a blade body can comprise an endoscopic cutting knife, which is can be used for cutting tissue using a piercing motion that moves approximately perpendicular to the tissue. As a third example, a blade body can comprise a punch and/or bite blade, which can be used for biopsies. As a fourth example, a blade body can comprise a drill bit, which can be used for dental and/or orthopedic procedures. In many embodiments, spine 110 can run along a top of blade body 102 until it reaches a portion of cutting wedge 101. In these or other embodiments, opposing faces 114 and 115 can extend down from spine 110 and/or up from cutting wedge 101. In many embodiments, a flat opposing face can have a variety of shapes and angles. For example, when a cutting instrument comprises an axe, its flat opposing faces can slope towards each other as they travel towards the axe's cutting wedge. As another example, when a cutting instrument comprises a saw, its flat opposing faces can remain approximately parallel to each other from the spine of the saw to the cutting wedge(s) of the saw. In many embodiments, slot 112 can be formed through blade body 102. In many embodiments, slot 112 can be configured for coupling a tang 11 formed at a free end of a handle 10 for securely engaging the handle 10 to blade body 102. In some embodiments, handle 10 can be a gripper, clamp, robotic arm, and/or another mechanism used to hold blade body 102. For example, when blade body 102 is used in a laparoscopic procedure, handle 10 can comprise one or more portions of a laparoscope.

In many embodiments, blade body 102 can comprise a cutting wedge 101. Generally speaking, a cutting wedge can be a portion of a blade body configured to cut and/or pierce (e.g., non-blunted portions of the blade body). In these or other embodiments, a cutting wedge can be approximately wedge and/or pyramid shaped, but, similar to blade body 102, other shapes can be implemented depending on an intended use for the specific cutting instrument. In various embodiments, cutting wedge 101 can comprise one or more of cutting fasciae 104 and 105, leading edge 106, and/or a point 108. In various embodiments, each of cutting fasciae 104 and 105 can be angularly-oriented relative to each other and/or relative to a vertical axis of cutting instrument 100 that extending through leading edge 106 and spine 110. In many embodiments, an angle between cutting fasciae 104 and 105 can be approximately 28 degrees or lower, though lower angle ranges may impact the durability of the cutting wedge due to increased fragility. In many embodiments, a blade body can have differently sized and shaped cutting fasciae on opposite sides of the blade body. For example, one fascia (or a sub element of the fascia (e.g., a bevel)) can have a larger height and/or width than the other fascia, whether by design or due to manufacturing variations. In further embodiments, opposing faces 114 and 115 and spine 110 can be opposite to cutting fasciae 104 and 105 along a direction of elongation of blade body 102. In these or other embodiments, opposing faces 114 and 115 and spine 110 can terminate into point 108.

In many embodiments, cutting fasciae 104 and 105 can extend parallel to a direction of elongation of blade body 102 and/or intersect to form a leading edge 106 for cutting (e.g., cutting tissue during a surgical procedure). Therefore, in some embodiments, cutting fasciae can extend approximately perpendicular to (or at another angle to) a direction of elongation of the blade body. In other embodiments, cutting fasciae can extend in a non-parallel direction to a direction of elongation of the blade body, such as, for example, in blades used in laparoscopy and other minimally invasive surgery.

In some embodiments, cutting fasciae 104 and 105 can be identical in angular orientation relative to each other and/or relative to opposing faces 114 and 115, body 102, and/or surface topography of cutting instrument 100. In other embodiments, cutting fasciae 104 and 105 can have differing angular orientations and/or shapes from each other and/or relative to opposing faces 114 and 115, body 102, and/or surface topography of cutting instrument 100. For example, one or more of cutting fasciae 104 or 105 can be flat, slightly concave, or slightly convex. As noted above, leading edge 106 can be formed at an intersection of cutting fasciae 104 and 105. In these or other embodiments, leading edge 106 can have an overall surface topography that is a combined projection of topographies of cutting fasciae 104 and 105. In many embodiments, one cutting fascia can have a larger height and/or width than other cutting fascia on the same blade, whether by design, due to manufacturing variations, or due to wear. For example, as described in further detail below, many different combinations and permutations of cutting fascia can also be used. In some embodiments leading edge 106 can be curved or straight. The spine 110 may also be curved or straight, depending on the desired application of the cutting instrument 100. In some embodiments, the cutting fasciae 104 and 105 define an upper border 124 that distinguishes the cutting fasciae 104 and 105 from each of the opposing faces 114 and 115 of the blade body 102. In many embodiments, upper border 124 also defines a portion of an outer perimeter of cutting wedge 101.

In many embodiments, blade body 102 of cutting instrument 100 can comprise a metal suitable for surgical applications (e.g., an iron alloy comprising at least one other element including nickel, cobalt, carbon, and chromium such as stainless steel or carbon steel). In some embodiments, cutting fasciae 104 and 105 of blade body 102 can comprise a non-metal (e.g., ceramic, diamond, or sapphire). In some embodiments, cutting instrument 100 can be treated with an anti-microbial coating or finish to further reduce a risk of surgically induced infections. In the same or different embodiments, cutting instrument 100 (and particularly, cutting fasciae 104 and 105) also can be coating with one or more conformal or non-conformal coatings.

Turning now to FIGS. 3A-3F, exemplary a cross-sectional views through various blade bodies are shown. As shown in FIGS. 3A-3F, a blade body can have different shapes and/or configurations. In many embodiments, various elements of FIGS. 3A-3F can be interchanged by a person having ordinary skill in the art. For example, a blade body can include cutting fascia 104 (FIG. 3A) on one side of the blade body and can include cutting fascia 505 (FIG. 3E) on an opposite side of the blade body.

Figure 3C:
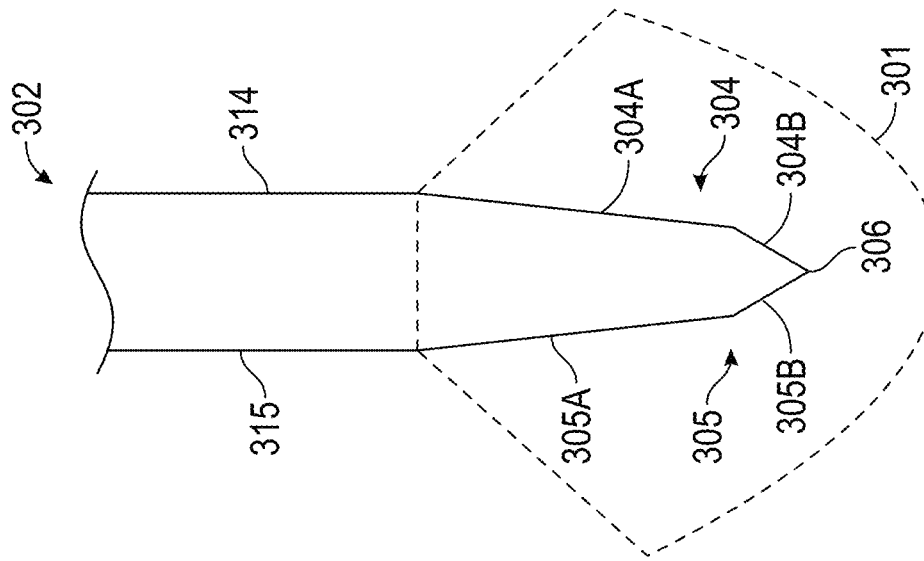
FIGS. 3A-3F show exemplary cross-sectional views of various blade bodies.
Figure 3B:
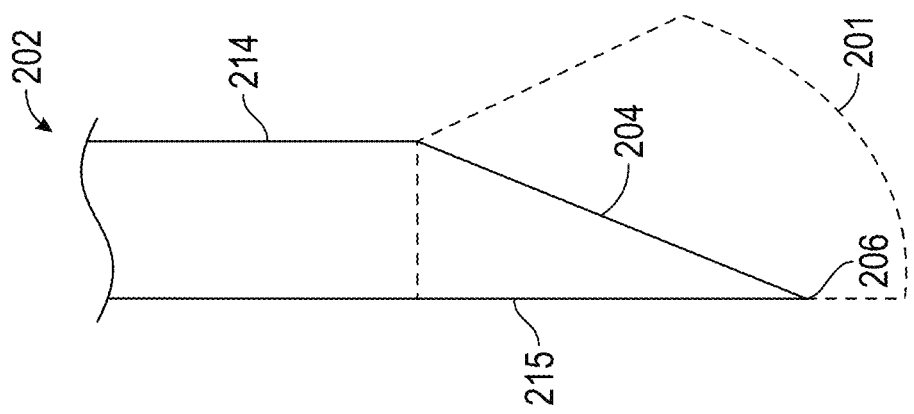
Figure 3A:
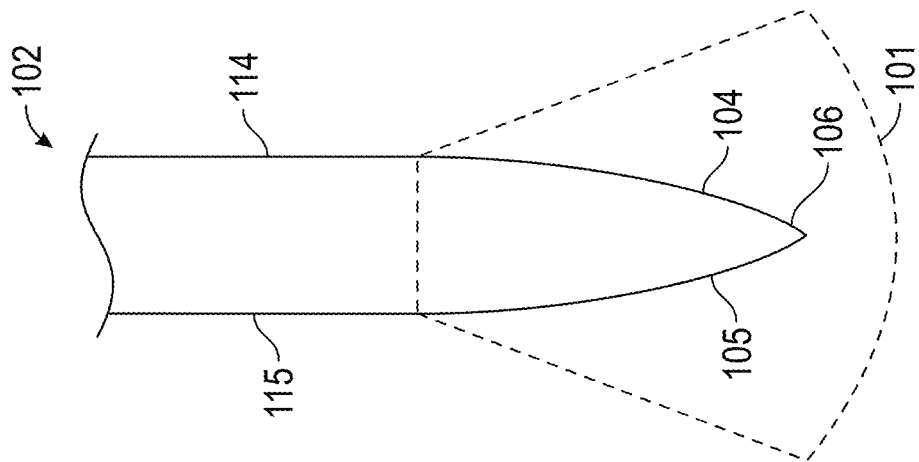

Turning now to FIG. 3A, a cross section of cutting instrument 100 through blade body 102 at cross-sectional line 301 (FIG. 1) is shown. As shown in FIG. 3A, cutting wedge 101 can have an approximately triangular cross section with slightly arced/rounded sides. In many embodiments, blade body 102 can be referred to as a single bevel embodiment because it has only one bevel in its cutting wedge 101. Cutting fasciae 104 and 105 can also be seen curvedly sloping inward (e.g., in a concave direction) from opposing faces 114 and 115 to leading edge 106.

Turning now to FIG. 3B, a cross section of blade body 202 is shown. In many embodiments, blade body 202 can comprise cutting wedge 201 and opposing faces 214 and 215. In further embodiments, cutting wedge 201 can comprise cutting fascia 204 and leading edge 206. In many embodiments, blade body 202 can be referred to as a single fascia embodiment because it has only one cutting fascia 204. In these or other embodiments, opposing face 215 can extend from a spine (not pictured) to leading edge 206 without a second cutting fascia in between the spine and leading edge 206. In many embodiments, blade body 202 can be used as a chisel or with another cutting motion using a similar application of force.

Turning now to FIG. 3C, a cross section of blade body 302 is shown. In many embodiments, blade body 302 can comprise cutting wedge 301 and opposing faces 314 and 315. In these or other embodiments, cutting wedge 301 can comprise cutting fasciae 304 and 305 and a leading edge 306. In many embodiments, cutting fasciae 304 and 305 can comprise first bevels 304A and 305A and second bevels 304B and 305B. In these or other embodiments, blade body 302 can be referred to as a double bevel and/or a compound bevel embodiment because it has two sets of bevels. While blade body 302 is shown as having two sets of bevels, it will be understood that other embodiments can have only one set of bevels, or three or more sets of bevels. For example, in some embodiments, opposing face 315 can extend down from a spine (not pictured) to leading edge 306 without cutting fascia 305 (similarly to opposing face 215 (FIG. 3B)) between the spine and leading edge 306. In many embodiments, first bevels 304A and 305A can extend downward from opposing faces 314 and 315 to second bevels 304B and 305B. In these or other embodiments, second bevels 304B and 305B can meet to form leading edge 306. In further embodiments, first bevels 304A and 305A can be substantially straight while second bevels 304B and 305B can be curved (or vice versa). A double bevel embodiment can have a number of advantage over single or no bevel embodiments. For example, a double bevel blade body can be much less prone to chipping or rolling than a single-bevel blade body because of the progressive taper of its cutting fasciae through multiple bevels.

Figure 3F:
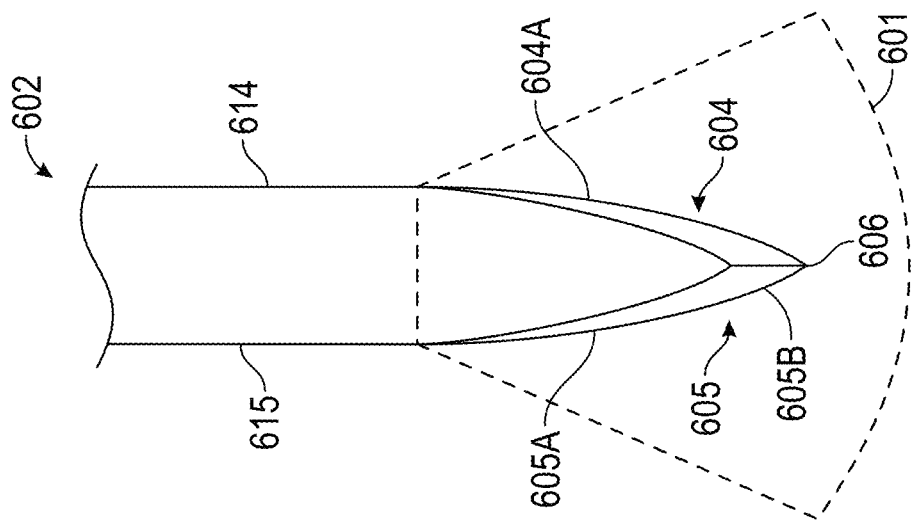
Figure 3E:
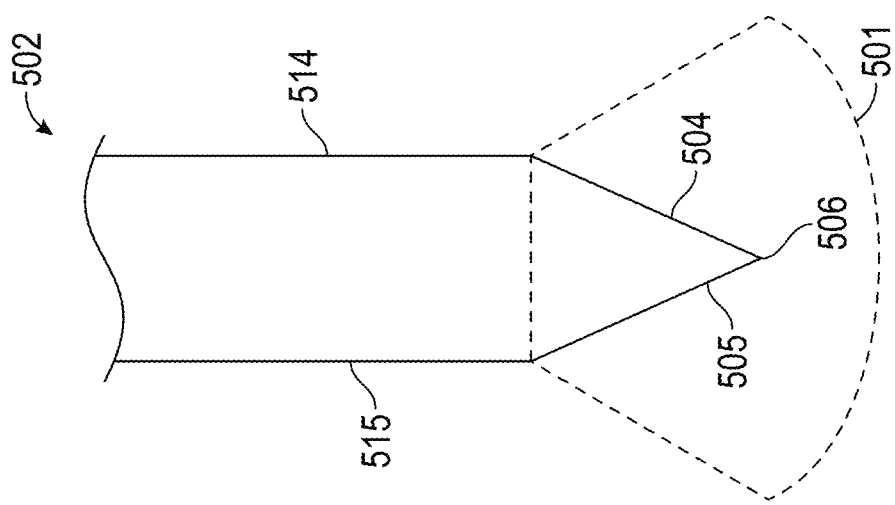
Figure 3D:
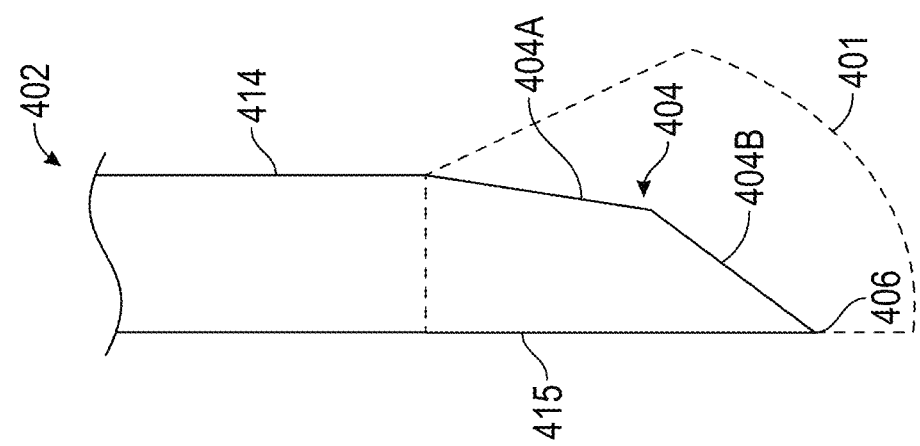

Turning now to FIG. 3D, a cross section of blade body 402 is shown. In many embodiments, blade body 402 can comprise a cutting wedge 401 and opposing faces 414 and 415. In further embodiments, cutting wedge 401 can comprise a cutting fascia 404 and a leading edge 406. In many embodiments, cutting fascia 404 can comprise first bevel 404A and second bevels 404B. In these or other embodiments, blade body 402 can be referred to as a double bevel and/or a compound bevel embodiment because it has two of bevels. In these or other embodiments, opposing face 415 can extend from a spine (not pictured) to leading edge 406 without a second cutting fascia the spine and leading edge 406. In many embodiments, blade body 402 can be used as a chisel or with another cutting motion using a similar application of force.

Turning now to FIG. 3E, a cross section of blade body 502 is shown. In many embodiments, blade body 502 can comprise a cutting wedge 501 and opposing faces 514 and 515. In further embodiments, cutting wedge 501 can comprise cutting fasciae 504 and 505 and a leading edge 506. In some embodiments, cutting fasciae 504 and 505 extend downward and meet at leading edge 506. In various embodiments, cutting fasciae 504 and 505 can be straight instead of curved (such as cutting fasciae 104 and 105 (FIGS. 1-3A)).

Turning now to FIG. 3F, a cross section of blade body 602 is shown. In many embodiments, blade body 602 can comprise cutting wedge 601 and opposing faces 614 and 615. In these or other embodiments, cutting wedge 601 can comprise cutting fasciae 604 and 605 and a leading edge 606. In many embodiments, cutting fasciae 604 and 605 can comprise first bevels 604A and 605A and second bevels 604B and 605B. In these or other embodiments, blade body 602 can be referred to as a double bevel and/or a compound bevel embodiment because it has two sets of bevels. While blade body 602 is shown below is shown having two sets of bevels, it will be understood that other embodiments can have only one set of bevels or three or more sets of bevels. For example, in some embodiments, opposing face 615 can extend down from a spine (not pictured) to leading edge 606 without cutting fascia 605 (similarly to opposing face 215 (FIG. 3B)). In many embodiments, first bevels 604A and 605A can extend downward from opposing faces 614 and 615 to second bevels 604B and 605B. In these or other embodiments, second bevels 604B and 605B can meet to form leading edge 606. In further embodiments, one or more of first bevel 604A, first bevel 605A, second bevel 604B, or second bevel 605B can be curved in either a convex or concave direction. In these embodiments, their radius of curvature can range from approximately 8,000 micrometers (μm) to 25,000 μm. In a particular embodiment, first bevels 604A and 605A are convex, as described above, and second bevels 604B and 605B are substantially straight and not curved, as described above. In this particular embodiment, the arc of curvature for first bevels 604A and 605A can be approximately 1,000-15,000 μm in length, and second bevels 604A and 605B can have a length of approximately 100 μm to 200 μm. In various embodiments, first bevels 604A and 605A and second bevels 604B and 605B can be blended together so that there is a smooth transition between the first and second bevels. In these or other embodiments, a transition between the bevels can comprise a sharp angle (e.g., such as in blade body 302 (FIG. 3C)). A double bevel embodiment can have a number of advantage over single or no bevel embodiments. For example, a double bevel blade body can be much less prone to chipping or rolling than a single-bevel blade because of the progressive taper of its cutting fasciae through multiple bevels.

In many embodiments not shown in FIGS. 3A-3F, a cross section of a blade body can have a cylindrical shape (e.g., when a punch and/or bite blade is used). In these embodiments, opposing sides of a blade body can comprise an interior and an exterior of the cylinder. In various embodiments, cutting fascia of a cylindrical cross section blade can slope towards a circular leading edge. In some embodiments, a blade body can be shaped in an approximately hemispherical shape to form a "jaw" of a bite blade. In these embodiments, opposing sides can be on an interior and an exterior of the hemisphere. In various embodiments, cutting fascia of a bite blade can slope towards an arcuate leading edge.

Returning now to FIGS. 1 and 2, a termination of cutting fasciae 104 and 105 at an edge of blade body 102 can define leading edge 106 of cutting instrument 100. As described above, the cutting fasciae 104 and 105 (and by association leading edge 106) can be curved (e.g., concave or convex) or straight. In some embodiments, a cutting wedge described herein (e.g., cutting wedge 101) can have an improved surface topography that is quantifiably uniform and has fewer imperfections (e.g., serrations, voids, or residual grind marks, etc.) than a cutting wedge on a standard blade body. In various embodiments, an improved cutting wedge surface topography can be created by removing material, adding material, or both performed either sequentially or simultaneously. In many embodiments, an improved cutting wedge surface topography can provide for a number of advantages. For example, an improved cutting wedge surface topography can provide for:

(i) Greater precision for exact incision placement;
(ii) Minimization of micro-tearing of tissue (or cracking in the case of bone) and associated undue trauma and excess bleeding, which can elongate the healing process;
(iii) Elimination of defect sites for tissue caking and serration fold-over resulting in more durable cutting instruments;
(iv) Elimination of weakened material sites reducing the tendency to fracture when contacting bone or other hard structures; and
(v) More consistent cutting instrument performance from blade to blade and blade manufacturing lot to blade manufacturing lot.

The above referenced improvements and other improvements described herein align with Halsted's principles of surgical technique that emphasizes gentle tissue handling for optimal clinical outcomes, and are therefore desirable in a number of instances.

Turning now to FIGS. 4-7, plurality of exemplary infographic illustrations detailing various areal field parameters are shown. Generally speaking, areal field parameters, which include areal height parameters, are a class of measurements used to quantify surface roughness for a variety of surfaces. Areal field parameters can be measured in a variety of ways. For example, a stylus can be placed on or dragged across a surface, and a displacement of the stylus can be measured and then mapped. As another example, a laser can be shone on a surface, and the laser's reflection off the surface can then be used to determine a height of various nanoscale surface features and properties as well as other properties (e.g., curvature).

Figure 4:
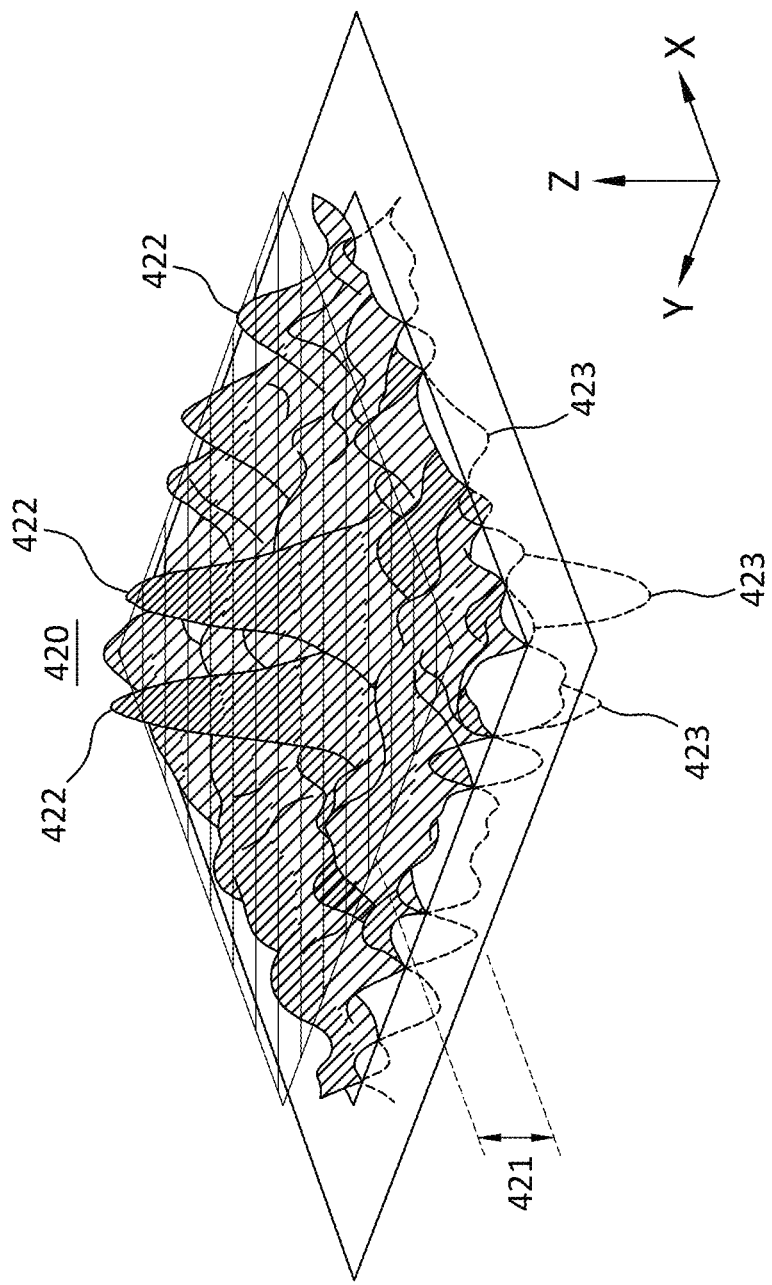
FIG. 4 shows an exemplary infographic illustration detailing an areal height parameter used to measure and visualize surface roughness of a cutting instrument.

Turning now to FIG. 4, an exemplary infographic illustration 420 detailing an areal height parameter 421 is shown. In many embodiments, areal height parameter 421 can comprise arithmetic mean height ($S_a$). In these or other embodiments, $S_a$ can comprise an arithmetic mean height of an absolute ordinate Z (x, y) (e.g., a Z height in an X, Y plane) across a measurement area (e.g., a 129 μm×129 μm area along a blade's cutting fascia). In various embodiments, arithmetic mean height can be calculated using an equation comprising:

$$S_a = \frac{1}{A} \int\int_A |Z(x,y)| dxdy$$

In these or other embodiments, $S_a$ can comprise a combined measurement area of the reading. In other words, $S_a$ comprises an arithmetic mean height of a plurality of nanoscale peaks 422 and valleys 423 that are detected on a surface. A standard deviation (u) of an arithmetic mean height on a surface can also be calculated so that surface roughness variation can be better understood. In various embodiments, standard deviation of an arithmetic mean height ($S_a$) can be calculated using an equation comprising:

$$\sigma = \sqrt{\left(\sum_{i=1}^{m}(X_{si} - S_a)^2\right)/(m-1)}$$

In these or other embodiments, m is representative of a number of profile elements encountered along the sampling length and $X_{si}$ is representative of a length of an i-th profile element. A low standard deviation of arithmetic mean height indicates low variability across a blade body, thereby leading to high blade body uniformity, high blade body smoothness, and a substantial reduction of serrations, voids, and residual grind marks along the blade body.

Although the photomicrographs shown in FIGS. 8A, 8B, 9A, 9B (discussed in more detail below) provide a visual comparison of surface topography between a standard blade and a blade having improved surface topography, a quantitative measure of the roughness between the blades can also be employed to measure surface roughness along areas of a cutting wedge.

Figure 5:
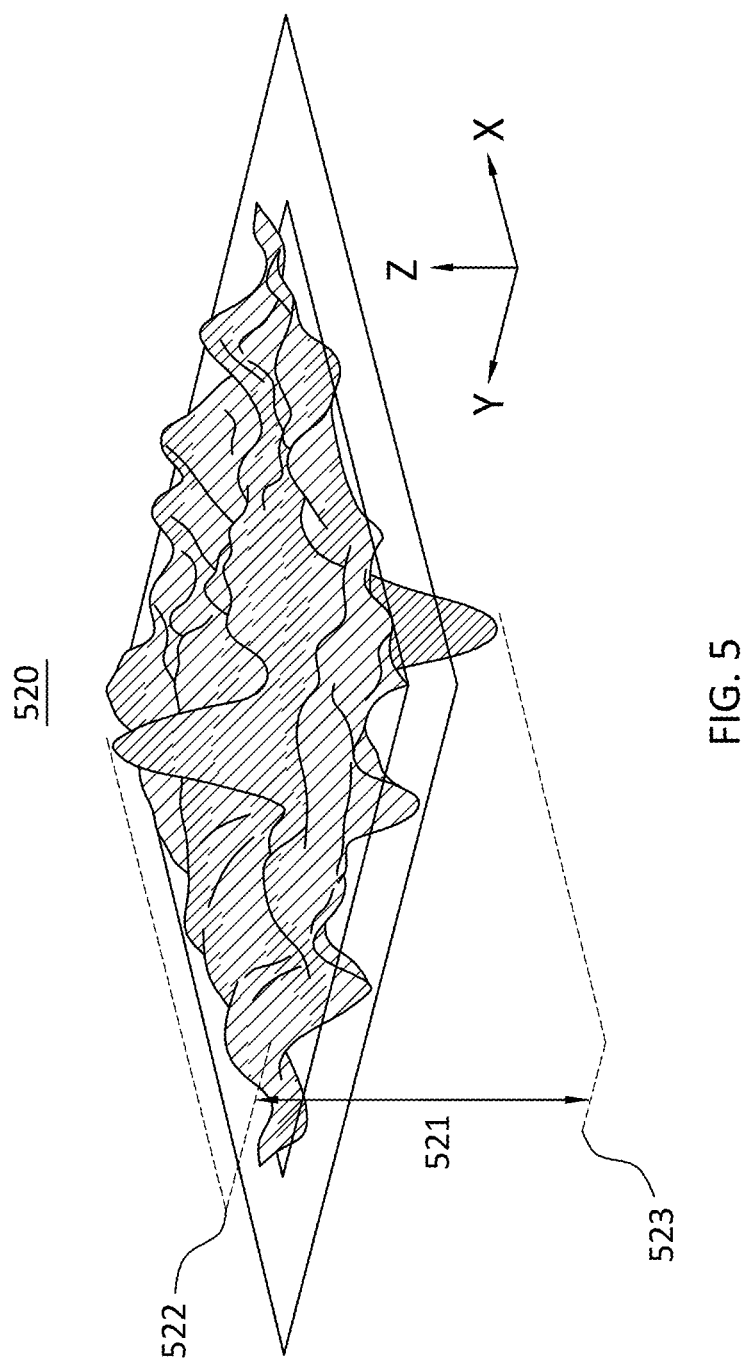
FIG. 5 is shows an exemplary infographic illustration detailing an areal function parameter used to measure and visualize surface roughness of a cutting instrument.

Turning now to FIG. 5, an exemplary infographic illustration 520 detailing an areal height parameter 521 is shown. As an example, areal height parameter 521 can be produced by the aforementioned Olympus OLS5000 3D Laser Scanning Confocal Microscope. In many embodiments, areal height parameter 521 can comprise a maximum height ($S_z$). In various embodiments, $S_z$ can comprise a sum of a largest peak height 522 ($S_p$) and a largest valley depth 523 ($S_v$) in a predefined measurement area. For example, a 129 μm×129 μm area can be measured.

A standard deviation (σ) of maximum height on a surface can also be calculated so that surface roughness variation can be better understood. In various embodiments, standard deviation of maximum height ($S_z$) can be calculated using an equation comprising:

$$\sigma = \sqrt{\left(\sum_{i=1}^{m}(X_{si} - S_z)^2\right)/(m-1)}$$

In these or other embodiments, m is representative of a number of profile elements encountered along the sampling length and $X_{si}$ is representative of the length of an i-th profile element. A low standard deviation of maximum height indicates low variability across a blade body, thereby further indicating high surface uniformity and high surface smoothness with an absence of any serrations.

Figure 6:
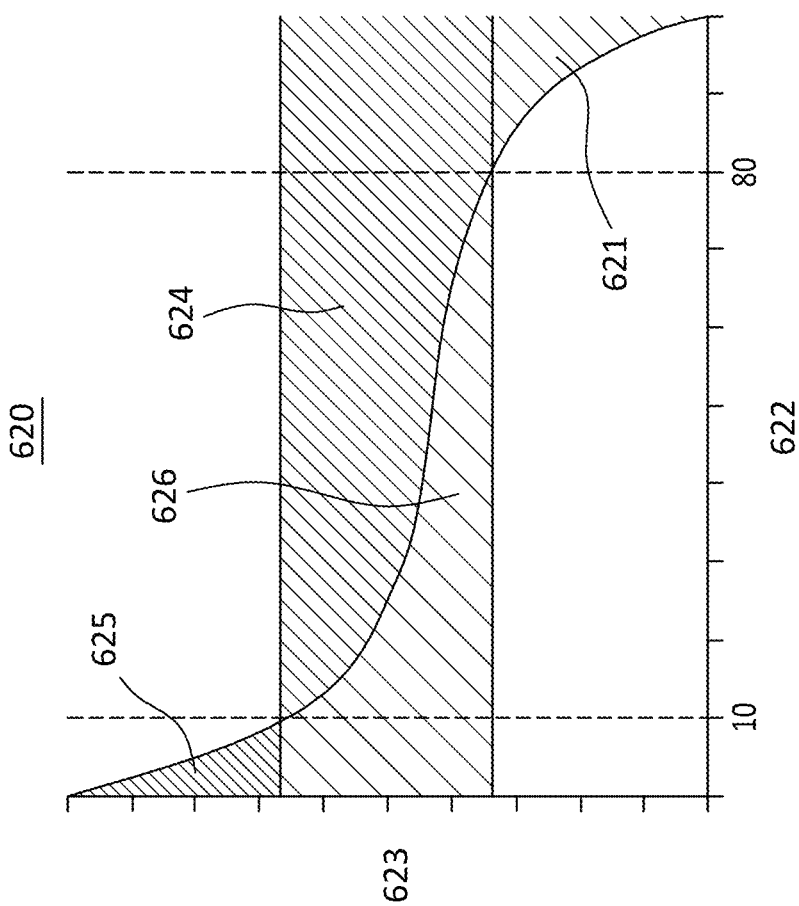
FIG. 6 is shows an exemplary infographic illustration detailing an areal function parameter used to evaluate and characterize surface roughness of a cutting instrument.

Turning now to FIG. 6, an exemplary infographic illustration 620 detailing an areal height parameter 621 is shown. As an example, areal height parameter 621 can be produced by the aforementioned Olympus OLS5000 3D Laser Scanning Confocal Microscope. In FIG. 6 the horizontal axis 622 can be a material ratio as a percentage, and the vertical axis 623 can be a height. In many embodiments, areal height parameter 621 can comprise a dale void volume ($V_{vv}$), otherwise known as a valley void volume. In various embodiments, $V_{vv}$ can comprise a volume of space bounded by a surface texture from a plane at a height corresponding to a specified material ratio level to a lowest valley on the surface. In many embodiments, a default value for a material ratio level can be 80%, but this value can be changed as needed. In various embodiments, $V_{vv}$ can be used to quantify the magnitude of the core surface, reduced peaks, and reduced valleys based on volume in an evaluation area. In many embodiments, a 129 μm×129 μm area can be measured. Other areal height parameters can also be seen in infographic illustration 620. For example, core void volume 624 ($V_{vc}$), peak material volume 625 ($V_{mp}$), and core material volume 626 ($V_{mc}$) can all be seen in infographic illustration 620. In many embodiments core void volume 624 can comprise a volume of space bounded by a surface at heights corresponding to material ratio values of "p" and "q." In these or other embodiments, peak material volume 625 can comprise volume of material at areal material ratio "p." In further embodiments, core material volume 626 can comprise a difference between the material volume at areal material ratio "q" and the material volume at areal material ratio "p." In various embodiments, material ratio volumes "p" and "q" can comprise 10% and 80%, respectively.

A standard deviation (σ) of dale void volume on a surface can also be calculated so that surface roughness variation can be better understood. In various embodiments, standard deviation of dale void volume ($V_{vv}$) can be calculated using an equation comprising:

$$\sigma = \sqrt{\left(\sum_{i=1}^{m}(X_{si} - V_{vv})^2\right)/(m-1)}$$

In these or other embodiments, m is representative of a number of profile elements encountered along the sampling length and $X_{si}$ is representative of the length of an i-th profile element. A low standard deviation of dale void volume indicates high surface uniformity and high surface smoothness with a substantial reduction of serrations, voids and residual grind marks along a cutting wedge.

Figure 7:
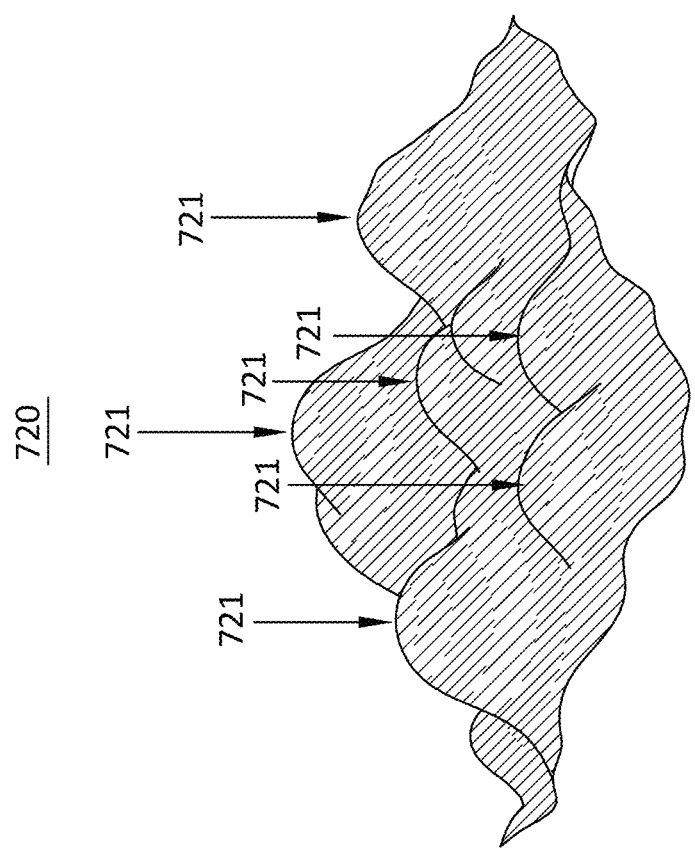
FIG. 7 shows an exemplary an infographic illustration detailing an areal feature parameter used to measure and visualize surface roughness of a cutting instrument.

Turning now to FIG. 7, an exemplary infographic illustration 720 detailing elements of an areal height parameter is shown. In many embodiments, an areal height parameter of infographic 720 can comprise an arithmetic mean peak curvature ($S_{pc}$). In various embodiments, $S_{pc}$ can comprise an arithmetic mean of a principal curvature of a plurality of peaks 721 on a surface. In various embodiments, a smaller value of $S_{pc}$ indicates that points of contact with other objects (e.g., tissue) have rounded shapes, while a larger value indicates that the points of contact with other objects have pointed shapes. In many embodiments, a 129 μm×129 μm area can be measured.

A standard deviation (σ) of arithmetic mean peak curvature on a surface can also be calculated so that surface roughness variation can be better understood. In various embodiments, standard deviation of arithmetic mean peak curvature can be calculated using an equation comprising:

$$\sigma = \sqrt{\left(\sum_{i=1}^{m}(X_{si}-S_{pc})^2\right)/(m-1)}$$

In these or other embodiments, m is representative of a number of profile elements encountered along the sampling length and $X_{si}$ is representative of the length of an i-th profile element. A low standard deviation of arithmetic mean peak curvature indicates high surface uniformity and high surface smoothness with a substantial reduction of serrations, voids and residual grind marks along a cutting wedge.

In many embodiments, uniformity of a cutting instrument having improved surface topography can be quantitatively defined as having an arithmetic mean height ($S_a$) of 150 nanometers (nm) or less, a standard deviation of arithmetic mean height ($S_a$) of 30 nanometers or less, a maximum height ($S_t$) of 1.5 micrometers or less, a standard deviation of maximum height ($S_t$) of 400 nanometers or less, a dale void volume ($V_{vv}$) of 0.02 μm$^3$/μm$^2$ or less, a standard deviation of dale void volume of 0.005 μm$^3$/μm$^2$ or less, an arithmetic mean peak curvature ($S_{pc}$) of 150 l/millimeter or less, and/or a standard deviation of arithmetic mean peak curvature of 30 l/millimeter or less. In this way, a cutting instrument having improved surface topography can have high surface uniformity, high surface smoothness, and an absence of serration along its cutting wedge.

Example 1

Figure 8B:
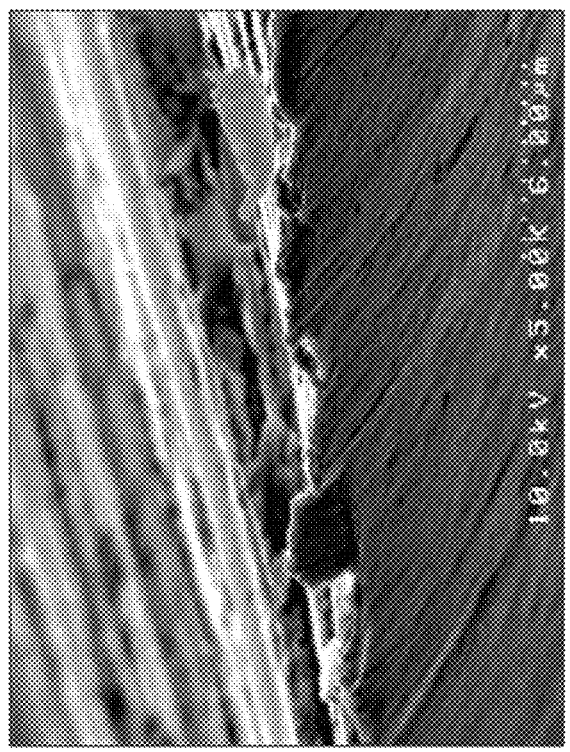
FIGS. 8A and 8B show exemplary scanning electron micrographs taken of a standard, unpolished cutting instrument.
Figure 8A:
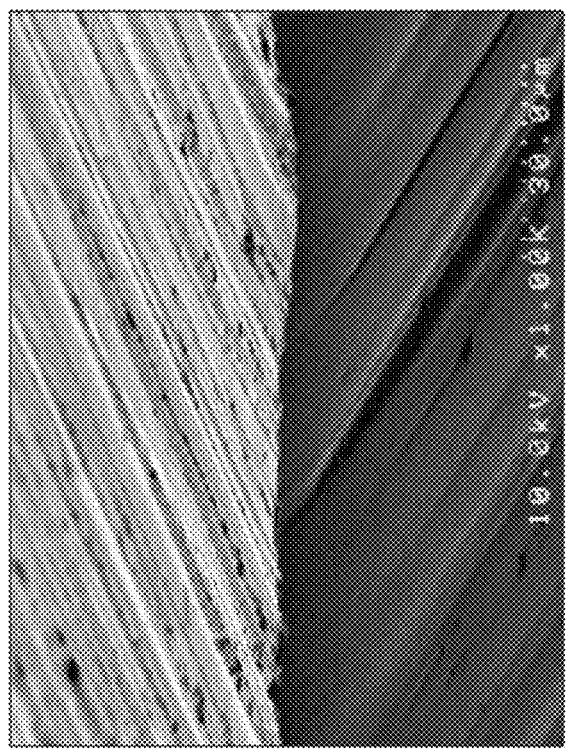

For experimental testing and comparison of cutting instruments, twenty standard Bard-Parker #15 scalpel blades, two of which are shown in FIGS. 8A and 8B were measured using an Olympus OLS5000 3D Laser Scanning Confocal Microscope. Three measurement areas, each 129 μm by 129 μm in size, were scanned on both sides of the Bard-Parker #15 scalpel blade at three different positions 1, 2 and 3 (FIGS. 13A-14B) along the scalpel. Blades shown in FIGS. 8A and 8B are standard blades with un-improved topography. The results showed that an average arithmetic mean height ($S_a$) on these three positions 1, 2, and 3 on each side of the Bard-Parker scalpel was measured to be 310 nm with a standard deviation of 171 nm; an average maximum height ($S_z$) was measured to be 2.862 μm with a standard deviation of 2.053 μm; an average dale void volume ($V_{vv}$) was measured to be 0.055 μm$^3$/μm$^2$ with a standard deviation of 0.037 μm$^3$/μm$^2$; and an average arithmetic mean peak curvature ($S_{pc}$) was measured to be 233.3 mm$^{-1}$ with a standard deviation of 416.4 mm$^{-1}$.

Figure 9B:
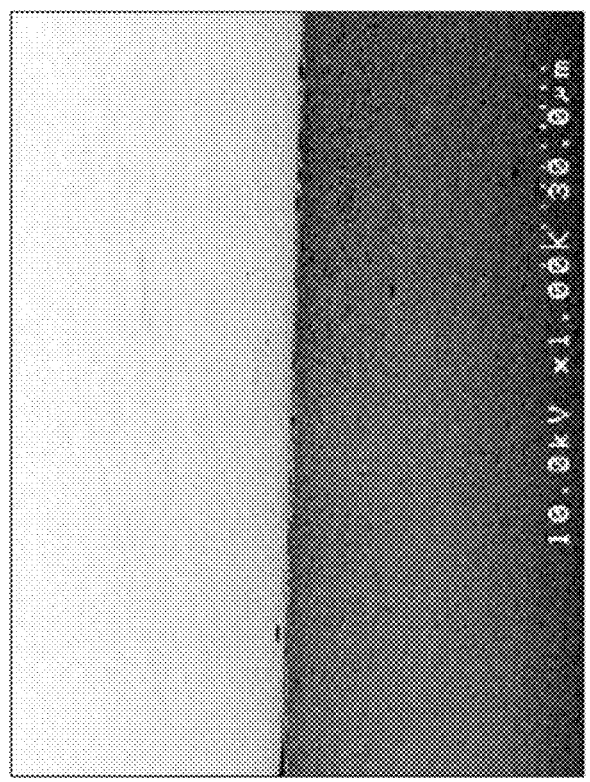
FIGS. 9A and 9B show exemplary scanning electron micrographs taken of a cutting instrument having improved surface topography, as described herein.
Figure 9A:
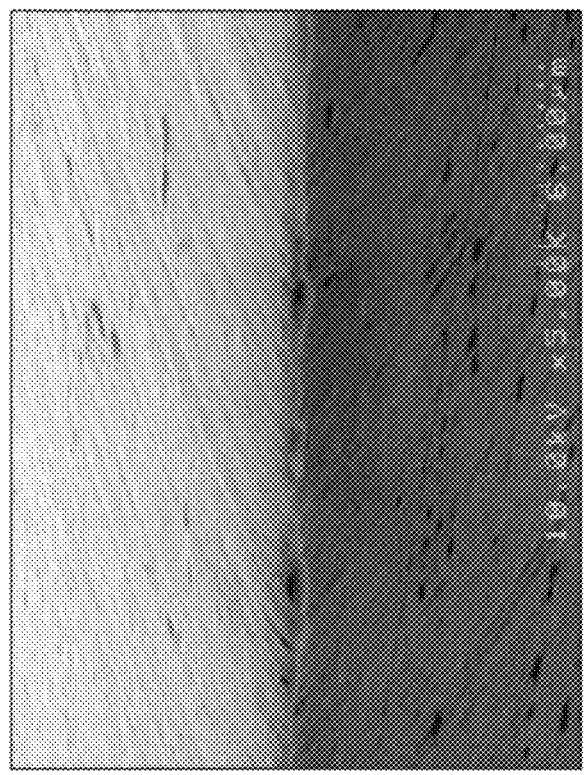

In contrast, twenty scalpels having improved topography, which appear in FIGS. 9A and 9B, were also measured using the 3D Laser Scanning Confocal Microscope after being processed using the techniques described herein. Three measurement areas, each 129 μm by 129 μm, were scanned at similar respective positions 1, 2 and 3 (FIGS. 14A-14B) along the scalpel having improved topography. The arithmetic mean height along these three positions was 91 nm or less on each of the samples measured, and had an average arithmetic mean height ($S_a$) of 32 nm with a standard deviation of 15 nm. These results display an 86% improvement in surface roughness and an 83% improvement in standard deviation. The largest maximum height ($S_z$) measured at these three positions per side was 1.401 μm or less on each of the samples measured, and had an average maximum height of 0.451 μm with a standard deviation of 0.22 μm, thereby demonstrating an 82% improvement in the surface roughness and a 91% improvement in standard deviation. The dale void volume ($V_{vv}$) at these three positions per side was 0.011 μm$^3$/μm$^2$ or less on each of the samples measured, and had an average dale void volume ($V_{vv}$) of 0.004 μm$^3$/μm$^2$ with a standard deviation of 0.002 μm$^3$/μm$^2$, thereby demonstrating an 89% improvement in the surface roughness and an 88% improvement in standard deviation. The arithmetic mean peak curvature ($S_{pc}$) on these three locations per side was 84.3 mm$^{-1}$ or less on each of the samples measured, and had an average arithmetic mean peak curvature of 36.5 mm$^{-1}$ with a standard deviation of 16.4 mm$^{-1}$, thereby demonstrating an 84% improvement in the surface roughness and a 96% improvement in standard deviation. As such, the reduced roughness of the cutting fasciae 104 and 105 having an edge profile and reduced variability within both the fasciae 104 and 105.

Example 2

Figure 10:
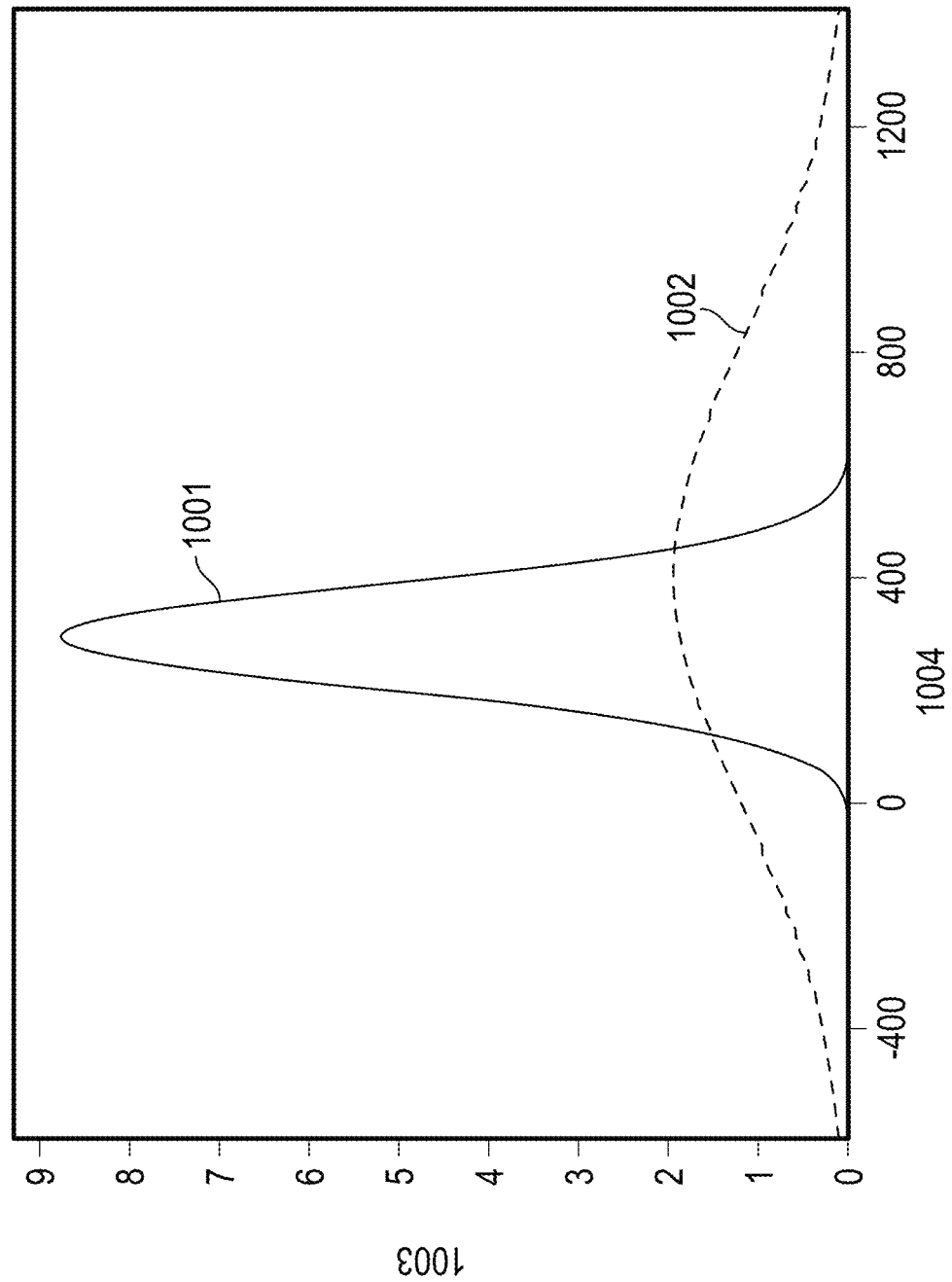
FIG. 10 shows an exemplary a frequency distribution diagram for scar widths comparing a standard cutting instrument with a cutting instrument having improved surface topography, as described herein.

FIG. 10 is a graphical representation that compares a performance of a scalpel having improved surface topography (Curve 1001) with a standard cutting blade (Curve 1002) when an incision was made in Duroc pig tissue, which is known to be a model for human scarring. Curve 1002 shows the distribution of ten scar widths 60 days subsequent to incision, when employing a standard scalpel having an average $S_a$ of 310 nm, an average $S_z$ of 2.862 μm, an average $V_{vv}$ of 0.055 μm$^3$/μm$^2$ and an average $S_{pc}$ of 233.3 mm$^{-1}$. Curve 1001, represents a similar set of data employing a scalpel having improved surface topography with an average arithmetical mean height $S_a$ of 32 nm, an average $S_z$ of 0.451 μm, an average $V_{vv}$ of 0.004 μm$^3$/μm$^2$ and an average $S_{pc}$ of 36.5 mm$^{-1}$. The width of the distribution curves is a direct measure of scar-to-scar variation. In surgical settings, it is desirable for incisions and scars generated by such incisions to be more repeatable and consistent. Thus, patient and surgeon will benefit from greater consistency and repeatability of the incision when using a scalpel having improved surface topography that exhibits a lower $S_a$, $S_z$, $V_{vv}$ and $S_{pc}$. Both Curve 1001 and Curve 1002 use the same axis 1003 and 1004. In various embodiments, axis 1003 can be referred to as a Y axis, and axis 1004 can be referred to as an X axis. In some embodiments, the X axis can comprise a number of occurrences, and/or the Y axis can comprise a scar width in μm.

Example 3

FIG. 11A shows a graphical representation that compares the performance of the blade body of the disclosed surgical cutting instrument with the improved surface topography (1102) with a standard cutting blade (1101) when an incision was made through a saphenous nerve in a guinea pig (*Cavia porcellus*). Measurement for both blades 1101 and 1102 use the same axis 1103 and 1104. In various embodiments, axis 1103 can be referred to as a Y axis, and axis 1104 can be referred to as an X axis. In some embodiments, the Y axis can comprise a percentage regeneration of a nerve based on a percent of pre-incision electrical impulse carried, and/or the X axis can comprise the specific blade used. As can be seen in FIG. 11A, nerves incised with blade 1102 show improved healing and pass more electrical impulses than nerves incised with blade 1101.

FIGS. 11B-11D are stained nerve images that illustrate nerve axon regeneration. The dark shaded areas in FIG. 11B show a normal nerve axon that has not been cut. FIG. 11C shows a nerve incised by a scalpel having improved surface topography, while FIG. 11D shows a nerve incised by a standard scalpel. Due to the dye applied to the slide, which binds to neurofilaments, darker shaded areas of a nerve represent improved nerve axon regeneration. As can be seen from FIGS. 11C and 11D, nerves cut with a scalpel having improved surface topography regenerate more efficiently, as can be seen by their darker color. In this way, any operation performed using a scalpel having improved surface topography can result in less post-operative nerve damage. After surgery, the degree of functional recovery relies on rapid regeneration of nerves to prevent irreversible muscle denervation. Nerves incised with a scalpel having improved surface topography showed a 25% recovery at five weeks while a nerve cut with a standard scalpel showed only 9% recovery. At 12 weeks, the nerves incised with a scalpel having improved surface topography showed a 92% recovery post-operatively while the standard scalpel showed less recovery. In the same study using guinea pig axons, advanced nerve stimulus detection technology was used to collect electrical impulse data from nerves incised with a scalpel having improved surface topography and a standard scalpel. The post-operative goal is for these nerves to recover to a minimum of 20% electrical conduction 5-8 weeks post-operatively. As depicted in FIG. 11A, the nerves incised with a scalpel having improved surface topography show a 25% recovery at five weeks versus a nerve cut with a standard scalpel showing less than 10% recovery.

Example 4

Figure 12:
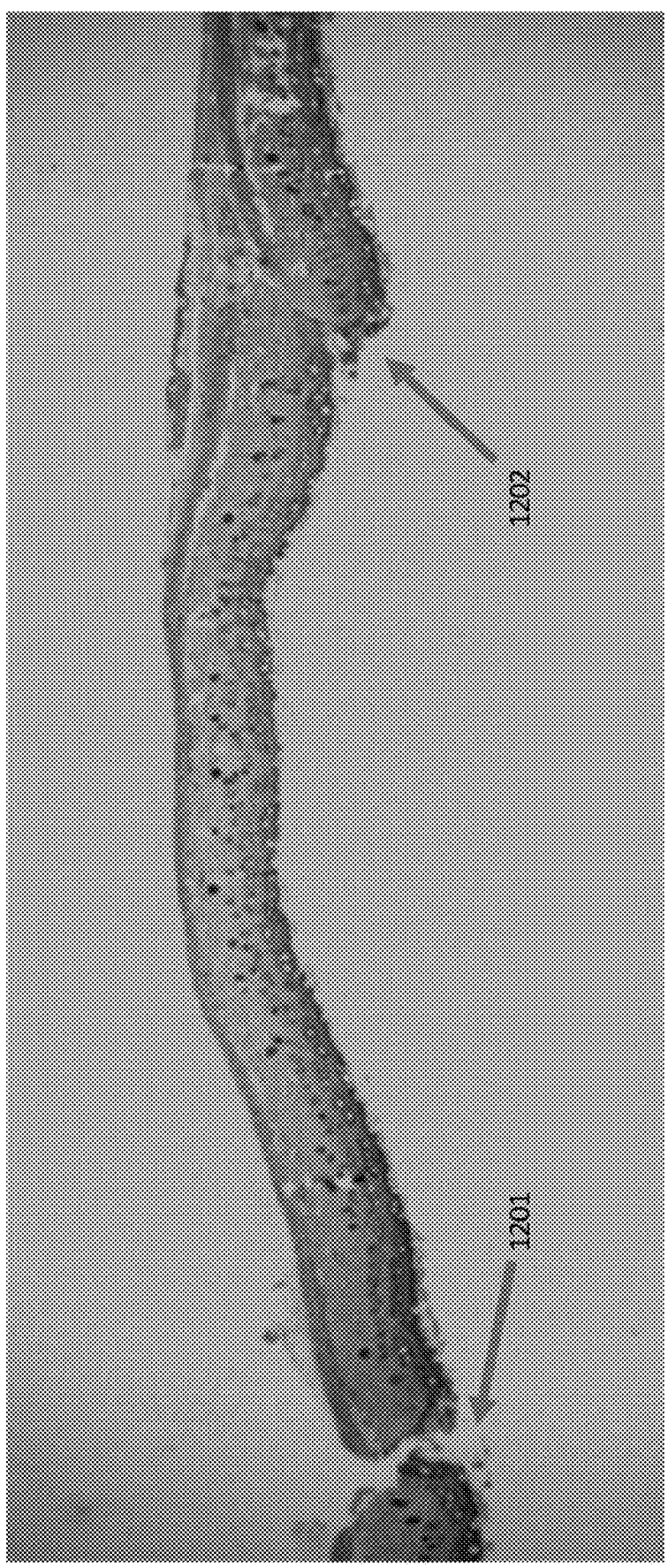
FIG. 12 shows an exemplary histological image representation of a *Cavia porcellus* sample.

FIG. 12 illustrates an example of histological studies performed using bilateral and approximately parallel incisions that show a more favorable post-operative wound healing when using a scalpel having improved surface topography 1202 versus a standard scalpel 1201. These studies show wound closure rates from a scalpel having improved surface topography incision at over 90% after just 24 hours while a standard scalpel showed only 10% during the same time period. The improved healing time is a result of minimizing surgically induced tissue trauma and the subsequent swelling which results from standard scalpels having high surface roughness properties. A scalpel having improved surface topography, on the other hand, creates less tissue trauma, which results in faster healing times and supports reduced surgical site infection risk.

Example 5

Figure 15:
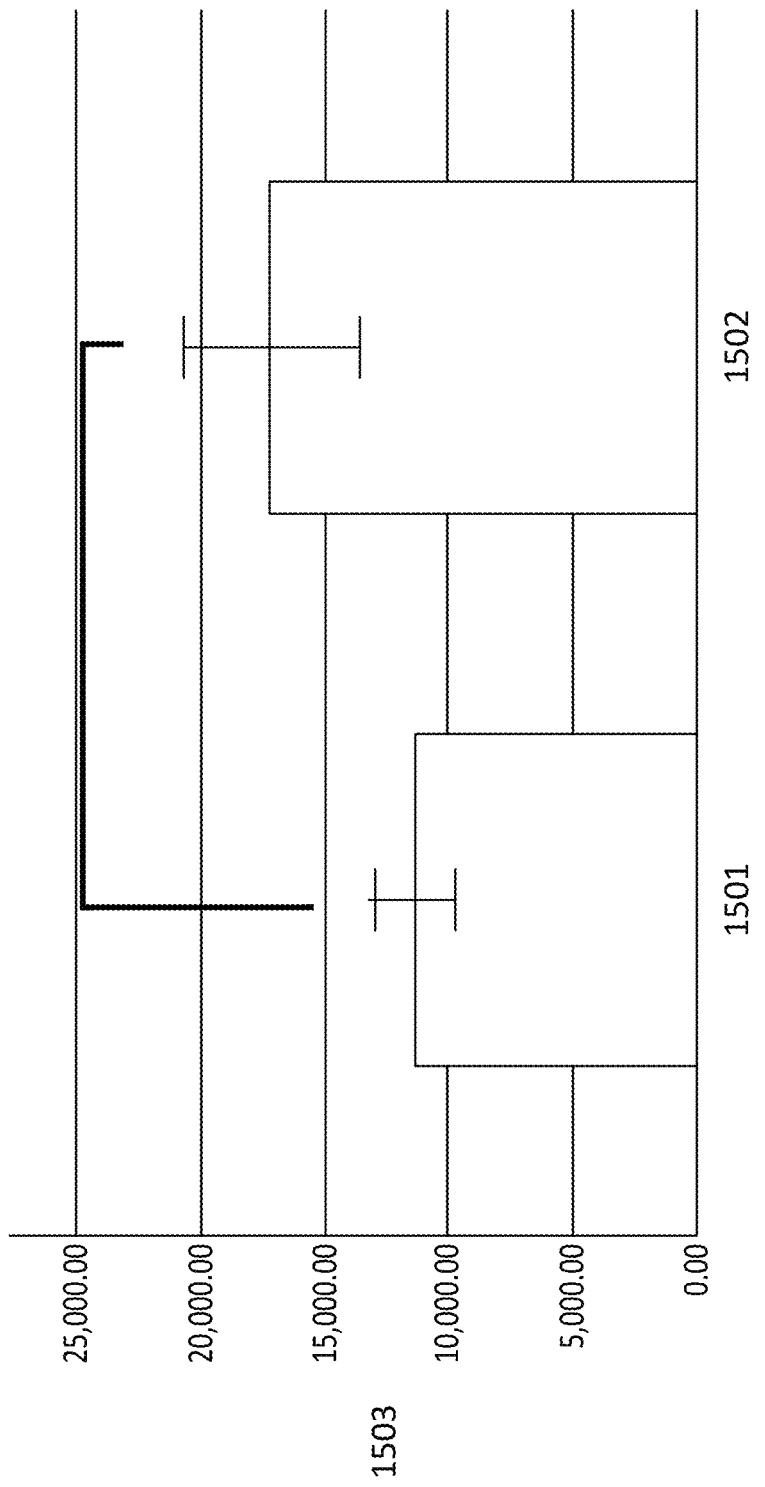
FIG. 15 shows an exemplary graphical representation comparing performance of a standard blade with a cutting instrument having improved surface topography.

In another study titled "Effect of an ultra-polished scalpel on incisional wounds in a diabetic rat model," the impact of using a scalpel having improved surface topography was compared to the standard scalpel compromised wound healing subjects. As can be seen in FIG. 15, scar areas were significantly lower in a scalpel having improved surface topography group 1501 (11,366 $\mu m^2 \pm 1,614$ $\mu m^2$) than in the conventional scalpel (CS or standard scalpel) group 1502 (17,189 $\mu m^2 \pm 3,583$ $\mu m^2$), p=0.028. The scalpel having improved surface topography group showed less inflammation at day 3 and significantly less TGF-β formation (days 3 and 7), and less collagen synthesis at day 7 than the CS group. The level of matrix metalloproteinase (MMPs) was also lower in the UPS group. This supports the conclusion that a scalpel having improved surface topography can achieve better healing creating less scar formation. Measurement for both scalpel groups 1501 and 1502 use the same axis 1503 and 1504. In various embodiments, axis 1503 can be referred to as a Y axis, and axis 1504 can be referred to as an X axis. In some embodiments, an X axis can comprise the specific blade used, and/or a Y axis can comprise a scar area measured in $\mu m^2$. As can be seen in FIG. 15, smaller scars are produced by incisions made with scalpel group 1501 compared to scalpel group 1502.

A number of methods can be employed to achieve uniformity of a cutting instrument having improved surface topography. For example, a cutting instrument having improved surface topography can be created by cleaving at least a single crystal from, or by over-plating, spin-coating, or depositing materials using chemical or physical vapor deposition onto, a blade body, including a cutting wedge of a blade body. Other possible methods of manufacture may include polishing of a cutting wedge, through electro-mechanical or chemical-mechanical processes, 3D printing, cold or hot working a metal into an edge absent grinding and like processes familiar to advanced metal working. In various embodiments, techniques for creating a cutting instrument having improved surface topography can be applied to only a portion of a cutting wedge. For example, the techniques described herein can be applied to only cutting fascia or a portion of the cutting fascia. In some embodiments, techniques described herein can be applied to a portion of a blade body most commonly used. For example, some surgeons only use a first quarter of a blade, as measured from a tip of the blade along a leading edge of the blade. In these embodiments, production costs can be saved by producing improved surface topography in only these high use areas of a cutting instrument. In various embodiments, the techniques described herein can extend or enlarge a size of cutting fascia up one or more opposing sides of a blade body towards the spine.

As stated above, one such method utilized to produce the disclosed cutting instrument is chemical-mechanical polishing (CMP), otherwise known as planarization. The process can begin by contacting cutting fascia with a polishing pad and a chemical-mechanical polishing composition. The polishing pad can be any suitable polishing pad, many of which are known in the industry. The polishing pad can have any suitable configuration. For example, the polishing pad can be circular and, when in use, have a rotational motion about an axis perpendicular to a plane defined by a surface of the pad. In other embodiments, a polishing pad can be cylindrical in shape, conical in shape, an endless belt, or any other suitable shape. In various embodiments, a polishing pad can have a reciprocating or orbital motion along a plane or semi-circle. Many other variations will be readily apparent to the skilled artisan. In some embodiments, a chemical-mechanical polishing composition can comprise particles of an abrasive and liquid, gel, or gel-like carrier. In these embodiments, the abrasive can be suspended in the carrier. Generally speaking, the abrasive can be any suitable abrasive material. Many types of abrasives will be readily apparent to the skilled artisan. Additional information on pads and/or compositions suitable for chemical-mechanical polishing can be found in U.S. Pat. No. 7,037,175, which is herein incorporated by this reference in its entirety.

The chemical-mechanical polishing process can be controlled to ensure the optimal utility of the disclosed cutting instrument. Due to the multitude of types and the complexity of shapes, each cutting fasciae may have different polishing process requirements. In many embodiments, a suitable polishing process can be achieved by controlling numerous variables of the process such as angle of polishing pad interface, rotational speed at interface, pressure of pad exerted on cutting fasciae, and indexing and dwell time at specific regions of the cutting fasciae. In various embodiments, CMP processes can be applied to a defective and/or rejected cutting instrument to produce a cutting instrument having an improved surface topography.

In various embodiments, particular care is required while polishing the cutting fascia as it transitions to an intersection of the fasciae (e.g., a leading edge). In some embodiments, a polishing apparatus (e.g., a CMP pad, a whetstone, fine grit sandpaper, etc.) cannot extend past a leading edge of a blade body to prevent dulling the cutting instrument (also known as "bullnosing" the blade). In many embodiments, after a cutting instrument is polished, a polymeric or diamond-like conforming coatings can be used to optimize tactile sensation of the cutting instrument when in use. In other embodiments, techniques can be used to prevent blunting and/or bullnosing a leading edge of a cutting instrument. In some embodiments, pressure applied to a blade via a polishing apparatus can be lightened as the polishing apparatus nears a leading edge such that the polishing apparatus is not deformed or bent around the leading edge to cause bullnosing of the leading edge when the polishing apparatus extends past the leading edge. In further embodiments, pressure applied to a blade via a polishing apparatus can remain steady across the entire fasciae when the polishing apparatus has a predetermined hardness such that the polishing apparatus is not deformed or bent around the leading edge to cause bullnosing of the leading edge when the polishing apparatus extends past the leading edge. For example, in these further embodiments, a polishing apparatus that is too hard to curve over or warp around a leading edge (e.g., a whetstone or hard CMP pad) can be used with a more steady, consistent, or greater pressure.

Figure 13A:
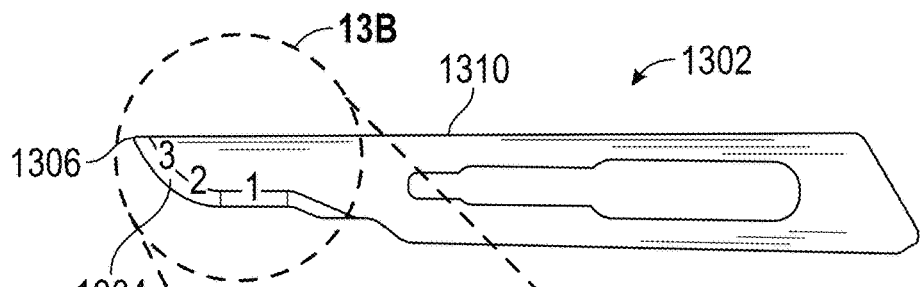
FIG. 13A-13B show exemplary enlarged views of a blade body.

Turning now to FIG. 13A, is a side view of a blade body 1302 is shown to have a cutting fascia 1304. In many embodiments, cutting fascia 1304 can comprise positions 1, 2, and 3 along blade body 1302 that were tested for surface roughness ($S_a$). Blade body 1302 is illustrated to show a leading edge 1306, an optional spine 1310, and an optional slot 1312.

Figure 13B:
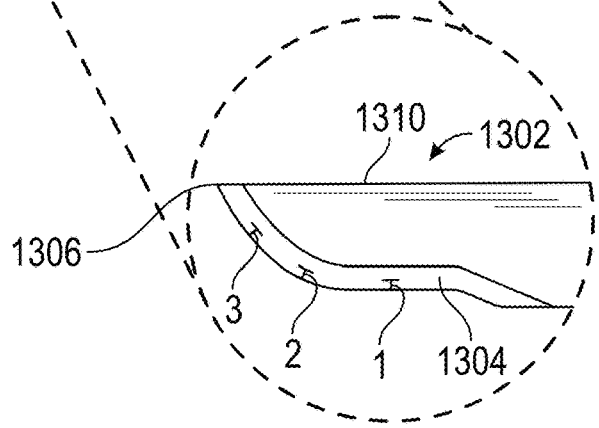

Turning now to FIG. 13B, an enlarged view of blade body 1302 of FIG. 13A is shown. In various embodiments, testing areas 1, 2, and 3 each measure 129 μm by 129 μm In various embodiments described in further detail in table 1, blades were tested for surface roughness ($S_a$, $S_z$, $V_{vv}$ and $S_{pc}$) at respective positions 1, 2, and 3 along their cutting fascia.

Figure 14A:
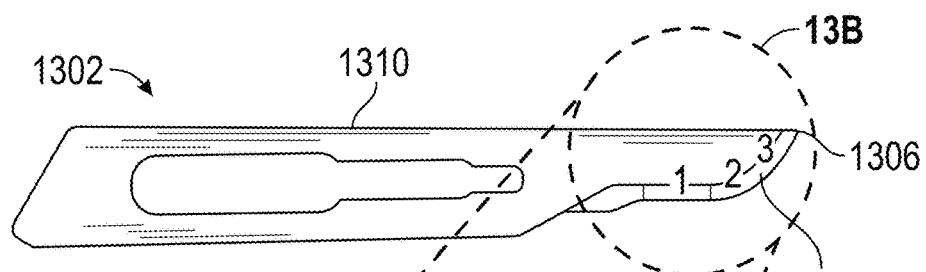
FIG. 14A-14B show exemplary enlarged views of an opposite side of the blade body of FIGS. 13A-13B.

Turning now to FIG. 14A, is an opposite side view of the blade body 1302 is shown to have a cutting fascia 1305. In many embodiments, cutting fascia 1305 can comprise positions 1, 2, and 3 along blade body 102 that were tested for surface roughness ($S_a$).

Figure 14B:
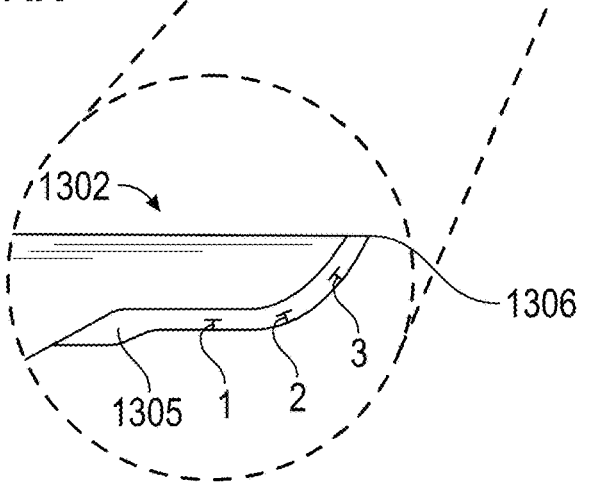

Turning now to FIG. 14B, an enlarged opposite side view of blade body 1302 of FIG. 14A is shown. In various embodiments, testing areas 1, 2, and 3 each measure 129 μm by 129 μm In various embodiments described in further detail in table 1, blades were tested for surface roughness ($S_a$, $S_z$, $V_{vv}$ and $S_{pc}$) at respective positions 1, 2, and 3 along their cutting fascia.

Table 1 provides the surface roughness data in terms of $S_a$, $S_z$, $V_{vv}$ and $S_{pc}$ for a blade body of a #15 scalpel having improved surface topography versus a prior art cutting instrument (a Bard-Parker #15 blade body). The $S_a$, $S_z$, $V_{vv}$ and $S_{pc}$ measurements were taken along each cutting fascia 1304 and 1305 at respective positions 1, 2, and 3 as shown in FIG. 13B and FIG. 14B. In various embodiments, each blade body having improved surface topography can have the measurements shown in Table 1 along 1% to 100% of its cutting wedge, where this 1% to 100% of the cutting wedge is referred to as the working portion. For example, the improved surface topography can be located on 25%, 50%, or 75% or more of the one or more cutting fasciae of the cutting wedge, where this 25%, 50%, or 75% or more of the one or more cutting fasciae would be referred to as the cutting wedge.

TABLE 1

| | Disclosed Cutting Instrument #15 | | | | | | Bard-Parker #15 | | | |
|---|---|---|---|---|---|---|---|---|---|---|
| No. | Desc. | Sz[μm] | Sa[μm] | Vvv[μm³/μm²] | Spc[1/mm] | No. | Desc. | Sz[μm] | Sa[μm] | Vvv[μm³/μm²] | Spc[1/mm] |
| 1 | 1A Pos 1 | 0.347 | 0.037 | 0.005 | 30.7 | 1 | 1A Pos 1 | 1.391 | 0.183 | 0.02 | 71.1 |
| 2 | 1A Pos 2 | 0.321 | 0.021 | 0.003 | 27.3 | 2 | 1A Pos 2 | 1.377 | 0.122 | 0.034 | 103.7 |
| 3 | 1A Pos 3 | 0.237 | 0.021 | 0.003 | 23.8 | 3 | 1A Pos 3 | 1.356 | 0.149 | 0.022 | 103.7 |
| 4 | 1B Pos 1 | 0.239 | 0.018 | 0.002 | 24.8 | 4 | 1B Pos 1 | 2.618 | 0.237 | 0.047 | 160.7 |
| 5 | 1B Pos 2 | 0.355 | 0.027 | 0.004 | 41.0 | 5 | 1B Pos 2 | 3.866 | 0.453 | 0.093 | 308.0 |
| 6 | 1B Pos 3 | 0.5 | 0.039 | 0.006 | 52.5 | 6 | 1B Pos 3 | 4.476 | 0.504 | 0.14 | 880.5 |
| 7 | 2A Pos 1 | 0.937 | 0.083 | 0.008 | 67.4 | 7 | 2A Pos 1 | 1.146 | 0.144 | 0.033 | 20.1 |

TABLE 1-continued

| # | Sample | | | | | # | Sample | | | | |
|---|---|---|---|---|---|---|---|---|---|---|---|
| 8 | 2A Pos 2 | 0.682 | 0.043 | 0.005 | 63.0 | 8 | 2A Pos 2 | 1.808 | 0.158 | 0.031 | 80.5 |
| 9 | 2A Pos 3 | 0.545 | 0.032 | 0.004 | 40.0 | 9 | 2A Pos 3 | 0.86 | 0.127 | 0.018 | 37.0 |
| 10 | 2B Pos 1 | 0.601 | 0.031 | 0.004 | 51.8 | 10 | 2B Pos 1 | 3.005 | 0.434 | 0.093 | 197.1 |
| 11 | 2B Pos 2 | 0.697 | 0.03 | 0.003 | 40.7 | 11 | 2B Pos 2 | 12.814 | 0.327 | 0.063 | 3526.5 |
| 12 | 2B Pos 3 | 0.798 | 0.078 | 0.007 | 82.4 | 12 | 2B Pos 3 | 5.364 | 0.262 | 0.05 | 788.3 |
| 13 | 3A Pos 1 | 0.556 | 0.038 | 0.004 | 43.6 | 13 | 3A Pos 1 | 1.238 | 0.245 | 0.016 | 150.1 |
| 14 | 3A Pos 2 | 0.813 | 0.091 | 0.011 | 74.4 | 14 | 3A Pos 2 | 1.392 | 0.165 | 0.029 | 17.4 |
| 15 | 3A Pos 3 | 0.803 | 0.058 | 0.006 | 48.9 | 15 | 3A Pos 3 | 1.556 | 0.219 | 0.031 | 22.4 |
| 16 | 3B Pos 1 | 1.401 | 0.062 | 0.004 | 66.7 | 16 | 3B Pos 1 | 2.244 | 0.254 | 0.036 | 165.3 |
| 17 | 3B Pos 2 | 0.496 | 0.045 | 0.004 | 41.1 | 17 | 3B Pos 2 | 4.674 | 0.839 | 0.129 | 174.1 |
| 18 | 3B Pos 3 | 0.417 | 0.025 | 0.004 | 27.0 | 18 | 3B Pos 3 | 3.614 | 0.51 | 0.092 | 174.5 |
| 19 | 4A Pos 1 | 0.258 | 0.019 | 0.003 | 23.5 | 19 | 4A Pos 1 | 1.132 | 0.193 | 0.016 | 53.9 |
| 20 | 4A Pos 2 | 0.49 | 0.063 | 0.006 | 32.9 | 20 | 4A Pos 2 | 1.055 | 0.159 | 0.019 | 7.4 |
| 21 | 4A Pos 3 | 0.326 | 0.027 | 0.004 | 23.4 | 21 | 4A Pos 3 | 2.13 | 0.141 | 0.019 | 22.0 |
| 22 | 4B Pos 1 | 0.902 | 0.043 | 0.004 | 62.5 | 22 | 4B Pos 1 | 2.881 | 0.378 | 0.086 | 200.0 |
| 23 | 4B Pos 2 | 0.65 | 0.067 | 0.006 | 51.9 | 23 | 4B Pos 2 | 4.543 | 0.638 | 0.096 | 437.0 |
| 24 | 4B Pos 3 | 0.551 | 0.048 | 0.005 | 45.5 | 24 | 4B Pos 3 | 4.487 | 0.671 | 0.178 | 232.8 |
| 25 | 5A Pos 1 | 0.614 | 0.019 | 0.003 | 20.5 | 25 | 5A Pos 1 | 0.886 | 0.133 | 0.02 | 61.9 |
| 26 | 5A Pos 2 | 0.324 | 0.034 | 0.005 | 19.6 | 26 | 5A Pos 2 | 1.936 | 0.189 | 0.038 | 108.6 |
| 27 | 5A Pos 3 | 0.24 | 0.024 | 0.003 | 25.2 | 27 | 5A Pos 3 | 2.624 | 0.214 | 0.04 | 414.2 |
| 28 | 5B Pos 1 | 0.5 | 0.04 | 0.005 | 43.8 | 28 | 5B Pos 1 | 3.453 | 0.496 | 0.075 | 237.5 |
| 29 | 5B Pos 2 | 0.614 | 0.044 | 0.004 | 58.4 | 29 | 5B Pos 2 | 3.781 | 0.5 | 0.113 | 227.7 |
| 30 | 5B Pos 3 | 0.733 | 0.045 | 0.006 | 57.3 | 30 | 5B Pos 3 | 4.82 | 0.333 | 0.065 | 344.0 |
| 31 | 6A Pos 1 | 0.203 | 0.017 | 0.002 | 18.9 | 31 | 6A Pos 1 | 2.232 | 0.356 | 0.049 | 15.0 |
| 32 | 6A Pos 2 | 0.269 | 0.021 | 0.003 | 29.6 | 32 | 6A Pos 2 | 1.009 | 0.111 | 0.016 | 31.1 |
| 33 | 6A Pos 3 | 0.21 | 0.016 | 0.002 | 22.5 | 33 | 6A Pos 3 | 1.153 | 0.14 | 0.02 | 42.3 |
| 34 | 6B Pos 1 | 0.575 | 0.041 | 0.007 | 61.8 | 34 | 6B Pos 1 | 2.22 | 0.454 | 0.036 | 131.6 |
| 35 | 6B Pos 2 | 0.402 | 0.033 | 0.005 | 50.0 | 35 | 6B Pos 2 | 3.079 | 0.309 | 0.06 | 168.5 |
| 36 | 6B Pos 3 | 0.595 | 0.055 | 0.008 | 71.9 | 36 | 6B Pos 3 | 3.55 | 0.476 | 0.121 | 217.9 |
| 37 | 7A Pos 1 | 0.253 | 0.022 | 0.003 | 28.7 | 37 | 7A Pos 1 | 1.746 | 0.23 | 0.033 | 65.1 |
| 38 | 7A Pos 2 | 0.241 | 0.018 | 0.003 | 24.0 | 38 | 7A Pos 2 | 1.391 | 0.159 | 0.026 | 52.4 |
| 39 | 7A Pos 3 | 0.379 | 0.03 | 0.005 | 50.8 | 39 | 7A Pos 3 | 1.036 | 0.152 | 0.021 | 29.1 |
| 40 | 7B Pos 1 | 0.363 | 0.027 | 0.005 | 39.3 | 40 | 7B Pos 1 | 3.285 | 0.427 | 0.103 | 159.5 |
| 41 | 7B Pos 2 | 0.587 | 0.045 | 0.008 | 74.7 | 41 | 7B Pos 2 | 5.119 | 0.588 | 0.1 | 214.7 |
| 42 | 7B Pos 3 | 0.729 | 0.052 | 0.008 | 84.3 | 42 | 7B Pos 3 | 3.134 | 0.454 | 0.077 | 164.8 |
| 43 | 8A Pos 1 | 0.395 | 0.032 | 0.005 | 45.5 | 43 | 8A Pos 1 | 1.027 | 0.074 | 0.016 | 63.6 |
| 44 | 8A Pos 2 | 0.354 | 0.03 | 0.004 | 30.7 | 44 | 8A Pos 2 | 1.139 | 0.153 | 0.025 | 52.3 |
| 45 | 8A Pos 3 | 0.359 | 0.045 | 0.007 | 36.9 | 45 | 8A Pos 3 | 1.422 | 0.189 | 0.048 | 18.1 |
| 46 | 8B Pos 1 | 0.724 | 0.041 | 0.003 | 40.6 | 46 | 8B Pos 1 | 7.491 | 0.301 | 0.037 | 809.6 |
| 47 | 8B Pos 2 | 0.276 | 0.031 | 0.003 | 8.9 | 47 | 8B Pos 2 | 4.432 | 0.37 | 0.073 | 280.8 |

TABLE 1-continued

| | | | | | | | | | | |
|---|---|---|---|---|---|---|---|---|---|---|
| 48 | 8B Pos 3 | 0.397 | 0.044 | 0.009 | 26.5 | 48 | 8B Pos 3 | 3.567 | 0.419 | 0.099 | 224.7 |
| 49 | 9A Pos 1 | 0.342 | 0.031 | 0.004 | 33.4 | 49 | 9A Pos 1 | 2.34 | 0.304 | 0.036 | 24.4 |
| 50 | 9A Pos 2 | 0.296 | 0.024 | 0.004 | 36.8 | 50 | 9A Pos 2 | 2.208 | 0.274 | 0.03 | 0.0 |
| 51 | 9A Pos 3 | 0.429 | 0.043 | 0.007 | 44.5 | 51 | 9A Pos 3 | 1.288 | 0.183 | 0.025 | 40.0 |
| 52 | 9B Pos 1 | 0.383 | 0.02 | 0.003 | 30.0 | 52 | 9B Pos 1 | 2.976 | 0.488 | 0.077 | 229.5 |
| 53 | 9B Pos 2 | 0.466 | 0.034 | 0.005 | 41.2 | 53 | 9B Pos 2 | 3.232 | 0.309 | 0.075 | 204.3 |
| 54 | 9B Pos 3 | 0.99 | 0.029 | 0.004 | 54.4 | 54 | 9B Pos 3 | 6.222 | 0.358 | 0.083 | 1426.1 |
| 55 | 10A Pos 1 | 0.272 | 0.019 | 0.003 | 24.7 | 55 | 10A Pos 1 | 2.277 | 0.31 | 0.032 | 127.2 |
| 56 | 10A Pos 2 | 0.258 | 0.021 | 0.002 | 27.1 | 56 | 10A Pos 2 | 1.088 | 0.141 | 0.025 | 67.7 |
| 57 | 10A Pos 3 | 0.301 | 0.019 | 0.003 | 28.7 | 57 | 10A Pos 3 | 1.168 | 0.224 | 0.02 | 40.3 |
| 58 | 10B Pos 1 | 0.498 | 0.037 | 0.004 | 35.7 | 58 | 10B Pos 1 | 3.22 | 0.486 | 0.093 | 199.3 |
| 59 | 10B Pos 2 | 0.705 | 0.034 | 0.004 | 33.2 | 59 | 10B Pos 2 | 6.171 | 0.74 | 0.093 | 595.5 |
| 60 | 10B Pos 3 | 0.547 | 0.051 | 0.008 | 33.7 | 60 | 10B Pos 3 | 5.607 | 0.506 | 0.143 | 325.8 |
| 61 | 11A Pos 1 | 0.222 | 0.014 | 0.002 | 18.9 | 61 | 11A Pos 1 | 0.936 | 0.137 | 0.018 | 55.7 |
| 62 | 11A Pos 2 | 0.131 | 0.016 | 0.002 | 7.6 | 62 | 11A Pos 2 | 0.805 | 0.146 | 0.017 | 23.0 |
| 63 | 11A Pos 3 | 0.195 | 0.016 | 0.002 | 18.0 | 63 | 11A Pos 3 | 1.595 | 0.104 | 0.015 | 70.6 |
| 64 | 11B Pos 1 | 0.316 | 0.022 | 0.003 | 13.1 | 64 | 11B Pos 1 | 3.637 | 0.497 | 0.078 | 280.0 |
| 65 | 11B Pos 2 | 0.307 | 0.027 | 0.005 | 9.0 | 65 | 11B Pos 2 | 4.844 | 0.709 | 0.171 | 454.1 |
| 66 | 11B Pos 3 | 0.256 | 0.022 | 0.003 | 9.7 | 66 | 11B Pos 3 | 3.045 | 0.379 | 0.103 | 180.2 |
| 67 | 12A Pos 1 | 0.62 | 0.034 | 0.003 | 38.4 | 67 | 12A Pos 1 | 1.275 | 0.213 | 0.035 | 81.6 |
| 68 | 12A Pos 2 | 0.69 | 0.031 | 0.003 | 43.2 | 68 | 12A Pos 2 | 1.096 | 0.151 | 0.027 | 92.9 |
| 69 | 12A Pos 3 | 0.231 | 0.015 | 0.002 | 17.0 | 69 | 12A Pos 3 | 1.209 | 0.121 | 0.02 | 83.0 |
| 70 | 12B Pos 1 | 0.299 | 0.026 | 0.005 | 14.7 | 70 | 12B Pos 1 | 3.729 | 0.674 | 0.085 | 210.2 |
| 71 | 12B Pos 2 | 0.216 | 0.016 | 0.002 | 6.7 | 71 | 12B Pos 2 | 4.187 | 0.702 | 0.124 | 276.6 |
| 72 | 12B Pos 3 | 0.309 | 0.022 | 0.004 | 25.1 | 72 | 12B Pos 3 | 2.584 | 0.28 | 0.044 | 206.7 |
| 73 | 13A Pos 1 | 0.255 | 0.015 | 0.002 | 22.1 | 73 | 13A Pos 1 | 0.824 | 0.108 | 0.02 | 20.4 |
| 74 | 13A Pos 2 | 0.199 | 0.014 | 0.002 | 17.4 | 74 | 13A Pos 2 | 1.08 | 0.137 | 0.021 | 13.6 |
| 75 | 13A Pos 3 | 0.197 | 0.014 | 0.002 | 18.3 | 75 | 13A Pos 3 | 1.09 | 0.123 | 0.03 | 34.8 |
| 76 | 13B Pos 1 | 0.161 | 0.016 | 0.002 | 5.2 | 76 | 13B Pos 1 | 3.729 | 0.427 | 0.068 | 610.2 |
| 77 | 13B Pos 2 | 0.131 | 0.013 | 0.002 | 5.5 | 77 | 13B Pos 2 | 4.167 | 0.314 | 0.097 | 202.6 |
| 78 | 13B Pos 3 | 0.245 | 0.015 | 0.003 | 17.9 | 78 | 13B Pos 3 | 5.049 | 0.35 | 0.086 | 308.5 |
| 79 | 14A Pos 1 | 0.532 | 0.028 | 0.004 | 37.3 | 79 | 14A Pos 1 | 1.731 | 0.158 | 0.018 | 89.5 |
| 80 | 14A Pos 2 | 0.242 | 0.021 | 0.002 | 24.6 | 80 | 14A Pos 2 | 2.132 | 0.206 | 0.025 | 182.7 |
| 81 | 14A Pos 3 | 0.227 | 0.013 | 0.002 | 13.6 | 81 | 14A Pos 3 | 2.686 | 0.206 | 0.039 | 145.3 |
| 82 | 14B Pos 1 | 0.491 | 0.026 | 0.003 | 30.2 | 82 | 14B Pos 1 | 2.772 | 0.419 | 0.078 | 187.5 |
| 83 | 14B Pos 2 | 0.203 | 0.017 | 0.002 | 17.6 | 83 | 14B Pos 2 | 4.843 | 0.374 | 0.051 | 358.8 |
| 84 | 14B Pos 3 | 0.542 | 0.025 | 0.006 | 29.6 | 84 | 14B Pos 3 | 1.974 | 0.261 | 0.028 | 154.3 |
| 85 | 15A Pos 1 | 0.557 | 0.039 | 0.005 | 34.6 | 85 | 15A Pos 1 | 1.513 | 0.199 | 0.053 | 24.3 |
| 86 | 15A Pos 2 | 0.303 | 0.016 | 0.002 | 23.5 | 86 | 15A Pos 2 | 1.477 | 0.166 | 0.039 | 55.0 |
| 87 | 15A Pos 3 | 0.722 | 0.023 | 0.003 | 37.5 | 87 | 15A Pos 3 | 1.064 | 0.137 | 0.026 | 43.8 |

TABLE 1-continued

| # | Blade Pos | Sz[μm] | Sa[μm] | Vvv[μm³/μm²] | Spc[1/mm] | # | Blade Pos | Sz[μm] | Sa[μm] | Vvv[μm³/μm²] | Spc[1/mm] |
|---|---|---|---|---|---|---|---|---|---|---|---|
| 88 | 15B Pos 1 | 0.735 | 0.039 | 0.006 | 43.4 | 88 | 15B Pos 1 | 4.602 | 0.461 | 0.091 | 811.0 |
| 89 | 15B Pos 2 | 0.417 | 0.033 | 0.003 | 34.5 | 89 | 15B Pos 2 | 2.922 | 0.364 | 0.068 | 230.3 |
| 90 | 15B Pos 3 | 0.454 | 0.05 | 0.005 | 35.7 | 90 | 15B Pos 3 | 2.35 | 0.307 | 0.053 | 117.9 |
| 91 | 16A Pos 1 | 0.586 | 0.038 | 0.003 | 40.2 | 91 | 16A Pos 1 | 2.852 | 0.126 | 0.019 | 215.2 |
| 92 | 16A Pos 2 | 0.675 | 0.055 | 0.004 | 42.4 | 92 | 16A Pos 2 | 5.368 | 0.43 | 0.049 | 110.4 |
| 93 | 16A Pos 3 | 0.447 | 0.024 | 0.003 | 29.2 | 93 | 16A Pos 3 | 3.222 | 0.311 | 0.041 | 66.6 |
| 94 | 16B Pos 1 | 0.313 | 0.029 | 0.004 | 21.2 | 94 | 16B Pos 1 | 2.566 | 0.346 | 0.033 | 176.6 |
| 95 | 16B Pos 2 | 0.552 | 0.031 | 0.006 | 34.0 | 95 | 16B Pos 2 | 6.872 | 0.735 | 0.121 | 1030.1 |
| 96 | 16B Pos 3 | 0.616 | 0.044 | 0.005 | 45.9 | 96 | 16B Pos 3 | 3.168 | 0.268 | 0.062 | 173.1 |
| 97 | 17A Pos 1 | 0.507 | 0.029 | 0.003 | 35.5 | 97 | 17A Pos 1 | 3.646 | 0.331 | 0.045 | 72.2 |
| 98 | 17A Pos 2 | 0.191 | 0.019 | 0.002 | 14.3 | 98 | 17A Pos 2 | 2.209 | 0.285 | 0.072 | 183.4 |
| 99 | 17A Pos 3 | 0.267 | 0.021 | 0.003 | 19.7 | 99 | 17A Pos 3 | 1.152 | 0.099 | 0.013 | 17.4 |
| 100 | 17B Pos 1 | 0.427 | 0.034 | 0.004 | 32.9 | 100 | 17B Pos 1 | 2.735 | 0.291 | 0.063 | 85.6 |
| 101 | 17B Pos 2 | 0.508 | 0.033 | 0.005 | 37.5 | 101 | 17B Pos 2 | 3.112 | 0.358 | 0.059 | 241.2 |
| 102 | 17B Pos 3 | 0.375 | 0.033 | 0.004 | 31.3 | 102 | 17B Pos 3 | 1.511 | 0.169 | 0.031 | 106.8 |
| 103 | 18A Pos 1 | 1.237 | 0.035 | 0.003 | 69.7 | 103 | 18A Pos 1 | 1.286 | 0.206 | 0.018 | 103.6 |
| 104 | 18A Pos 2 | 0.333 | 0.024 | 0.002 | 29.7 | 104 | 18A Pos 2 | 2.404 | 0.372 | 0.058 | 87.7 |
| 105 | 18A Pos 3 | 0.285 | 0.023 | 0.003 | 21.2 | 105 | 18A Pos 3 | 1.138 | 0.1 | 0.014 | 91.0 |
| 106 | 18B Pos 1 | 0.497 | 0.043 | 0.004 | 38.9 | 106 | 18B Pos 1 | 2.082 | 0.448 | 0.03 | 117.9 |
| 107 | 18B Pos 2 | 0.466 | 0.037 | 0.005 | 37.8 | 107 | 18B Pos 2 | 2.856 | 0.479 | 0.077 | 174.5 |
| 108 | 18B Pos 3 | 0.416 | 0.031 | 0.004 | 32.9 | 108 | 18B Pos 3 | 14.4 | 0.434 | 0.066 | 2211.5 |
| 109 | 19A Pos 1 | 0.459 | 0.033 | 0.004 | 26.6 | 109 | 19A Pos 1 | 1.12 | 0.123 | 0.022 | 69.9 |
| 110 | 19A Pos 2 | 0.241 | 0.021 | 0.003 | 25.0 | 110 | 19A Pos 2 | 1.609 | 0.273 | 0.029 | 65.3 |
| 111 | 19A Pos 3 | 0.325 | 0.034 | 0.006 | 24.9 | 111 | 19A Pos 3 | 1.805 | 0.144 | 0.034 | 66.5 |
| 112 | 19B Pos 1 | 0.486 | 0.045 | 0.005 | 38.1 | 112 | 19B Pos 1 | 2.744 | 0.241 | 0.065 | 113.9 |
| 113 | 19B Pos 2 | 0.567 | 0.046 | 0.007 | 35.4 | 113 | 19B Pos 2 | 5.154 | 0.45 | 0.117 | 379.6 |
| 114 | 19B Pos 3 | 0.507 | 0.039 | 0.009 | 29.9 | 114 | 19B Pos 3 | 3.112 | 0.363 | 0.075 | 168.6 |
| 115 | 20A Pos 1 | 0.277 | 0.032 | 0.004 | 24.0 | 115 | 20A Pos 1 | 0.935 | 0.136 | 0.019 | 21.5 |
| 116 | 20A Pos 2 | 0.274 | 0.026 | 0.003 | 23.1 | 116 | 20A Pos 2 | 1.321 | 0.121 | 0.03 | 13.3 |
| 117 | 20A Pos 3 | 0.274 | 0.036 | 0.003 | 26.8 | 117 | 20A Pos 3 | 2.222 | 0.155 | 0.022 | 174.1 |
| 118 | 20B Pos 1 | 0.59 | 0.028 | 0.004 | 39.7 | 118 | 20B Pos 1 | 2.187 | 0.326 | 0.046 | 143.4 |
| 119 | 20B Pos 2 | 0.602 | 0.03 | 0.003 | 40.5 | 119 | 20B Pos 2 | 4.162 | 0.61 | 0.096 | 274.1 |
| 120 | 20B Pos 3 | 0.612 | 0.053 | 0.01 | 38.5 | 120 | 20B Pos 3 | 5.223 | 0.592 | 0.13 | 285.6 |
| Count | | 120 | 120 | 120 | 120 | Count | | 120 | 120 | 120 | 120 |

| Disclosed #15 Blade | Sz[μm] | Sa[μm] | Vvv[μm³/μm²] | Spc[1/mm] | Bard-Parker #15 Blade | Sz[μm] | Sa[μm] | Vvv[μm³/μm²] | Spc[1/mm] |
|---|---|---|---|---|---|---|---|---|---|
| Average | 0.451 | 0.032 | 0.004 | 36.5 | Average | 2.862 | 0.31 | 0.055 | 233.3 |
| σ | 0.22 | 0.015 | 0.002 | 16.4 | σ | 2.053 | 0.171 | 0.037 | 416.4 |

Table 2 demonstrates the improved surface topography of the disclosed blade body 1302 by providing both an average and standard deviation of surface roughness in terms of $S_a$, $S_z$, $V_{vv}$ and $S_{pc}$ for a blade body of a #15 scalpel having improved surface topography versus a first prior art cutting instrument (a Bard-Parker #15 blade body or Standard Blade A), and versus a second prior art cutting instrument (a Swann-Morton #15 blade body or Standard Blade B). The $S_a$, $S_z$, $V_{vv}$ and $S_{pc}$ measurements were taken along the cutting fasciae at respective positions 1, 2, and 3 as shown in FIG. 13A and FIG. 14A. In various embodiments, each blade body having improved surface topography can have the measurements shown in Table 1 along 1% to 100% of its cutting wedge.

TABLE 2

|  | Sz (μm) | | Sa (μm) | | $V_{vv}$ ($\mu m^3/\mu m^2$) | | Spc (1/mm) | |
| --- | --- | --- | --- | --- | --- | --- | --- | --- |
|  | Avg | σ | Avg | σ | Avg | σ | Avg | σ |
| Disclosed Blade | 0.451 | 0.22 | 0.032 | 0.015 | 0.004 | 0.002 | 36.5 | 16.4 |
| Standard Blade A | 2.862 | 2.053 | 0.31 | 0.171 | 0.055 | 0.037 | 233.3 | 416.4 |
| Δ to Disclosed | 2.411 | 1.833 | 0.278 | 0.156 | 0.051 | 0.035 | 196.7 | 400.0 |
| % Reduction | 84% | 89% | 90% | 91% | 93% | 95% | 84% | 96% |
| Standard Blade B | 2.531 | 2.358 | 0.233 | 0.089 | 0.036 | 0.017 | 201.4 | 265.0 |
| Δ to Disclosed | 2.08 | 2.138 | 0.2 | 0.074 | 0.032 | 0.015 | 164.9 | 248.7 |
| % Reduction | 82% | 91% | 86% | 83% | 89% | 88% | 82% | 94% |

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto. For example, to one of ordinary skill in the art, it will be readily apparent that any element of FIGS. 1-15 may be modified, and that the foregoing discussion of certain of these embodiments does not necessarily represent a complete description of all possible embodiments.

All elements claimed in any particular claim are essential to the embodiment claimed in that particular claim. Consequently, replacement of one or more claimed elements constitutes reconstruction and not repair. Additionally, benefits, other advantages, and solutions to problems have been described with regard to specific embodiments. The benefits, advantages, solutions to problems, and any element or elements that may cause any benefit, advantage, or solution to occur or become more pronounced, however, are not to be construed as critical, required, or essential features or elements of any or all of the claims, unless such benefits, advantages, solutions, or elements are stated in such claim.

Moreover, embodiments and limitations disclosed herein are not dedicated to the public under the doctrine of dedication if the embodiments and/or limitations: (1) are not expressly claimed in the claims; and (2) are or are potentially equivalents of express elements and/or limitations in the claims under the doctrine of equivalents.

What is claimed is:

1. A cutting instrument, comprising:
   a blade body having two opposing faces and a cutting wedge comprising:
   a leading edge; and
   one or more cutting fasciae extending from at least one of the two opposing faces and defining at least a portion of the leading edge, wherein the one or more cutting fasciae have a surface roughness comprising:
   a measured arithmetic mean height ($S_a$) of 150 nm or less with a standard deviation of 30 nm or less across a measurement area of 16,641 square microns on at least a portion of the one or more cutting fasciae; and
   one or more of: (1) a measured maximum height ($S_t$) of 1.5 μm or less with a standard deviation of 0.4 μm or less within the measurement area of 16,641 square microns on the at least the portion of the one or more cutting fasciae; or (2) a measured arithmetic mean peak curvature ($S_{pc}$) of 150 mm$^{-1}$ or less with a standard deviation of 30 mm$^{-1}$ or less within the measurement area of 16,641 square microns on the at least the portion of the one or more cutting fasciae.

2. The cutting instrument of claim 1, wherein the surface roughness is formed into the one or more cutting fasciae using a process that removes material.

3. The cutting instrument of claim 2, wherein the process that removes the material comprises a chemical-mechanical polishing (CMP) process.

4. The cutting instrument of claim 2, wherein the process that removes the material uses a polishing pad that does not extend from one of the two opposing faces to beyond the leading edge.

5. The cutting instrument of claim 1, wherein the at least the portion of the one or more cutting fasciae comprises at least 50% of the one or more cutting fasciae.

6. The cutting instrument of claim 1, wherein:
   the surface roughness is formed into the one or more cutting fasciae using a process that removes material;
   the process that removes the material comprises a chemical-mechanical polishing (CMP) process;
   the process that removes the material uses a polishing pad that does not extend from one of the two opposing faces to beyond the leading edge; and
   the at least the portion of the one or more cutting fasciae comprises at least 50% of the one or more cutting fasciae.

7. A cutting instrument, comprising:
   a blade body having two opposing faces and a cutting wedge comprising:
   a leading edge; and
   one or more cutting fasciae extending from at least one of the two opposing faces and defining at least a portion of the leading edge, wherein the one or more cutting fasciae have a surface roughness comprising:
   a measured dale void volume ($V_{vv}$) of 0.02 μm$^3$/μm$^2$ or less with a standard deviation of 0.005 μm$^3$/μm$^2$ or less across a measurement area of 16,641 square microns on at least a portion of the one or more cutting fasciae; and
   one or more of: (1) a measured maximum height ($S_t$) of 1.5 μm or less with a standard deviation of 0.4 μm or less within the measurement area of 16,641 square microns on the at least the portion of the one or more cutting fasciae; or (2) a measured arithmetic mean peak curvature ($S_{pc}$) of 150 mm$^{-1}$ or less with a standard deviation of 30 mm$^{-1}$ or less within the measurement area of 16,641 square microns on the at least the portion of the one or more cutting fasciae.

8. The cutting instrument of claim 7, wherein the surface roughness is formed into the one or more cutting fasciae using a process that removes material.

9. The cutting instrument of claim 8, wherein the process that removes the material comprises a chemical-mechanical polishing (CMP) process.

10. The cutting instrument of claim 8, wherein the process that removes the material uses a polishing pad that does not extend from one of the two opposing faces to beyond the leading edge.

11. The cutting instrument of claim 7, wherein the at least the portion of the one or more cutting fasciae comprises at least 50% of the one or more cutting fasciae.

12. The cutting instrument of claim 7, wherein:
the surface roughness is formed into the one or more cutting fasciae using a process that removes material;
the process that removes the material comprises a chemical-mechanical polishing (CMP) process;
the process that removes the material uses a polishing pad that does not extend from one of the two opposing faces to beyond the leading edge; and
the at least the portion of the one or more cutting fasciae comprises at least 50% of the one or more cutting fasciae.

13. A cutting instrument, comprising:
a blade body having two opposing faces and a cutting wedge comprising:
a leading edge; and
one or more cutting fasciae extending from at least one of the two opposing faces and defining at least a portion of the leading edge, wherein the one or more cutting fasciae have a surface roughness comprising:
a measured arithmetic mean height ($S_a$) of 150 nm or less with a standard deviation of 30 nm or less across a measurement area of 16,641 square microns on at least a portion of the one or more cutting fasciae; and
a measured dale void volume ($V_{vv}$) of 0.02 $\mu m^3/\mu m^2$ or less with a standard deviation of 0.005 $\mu m^3/\mu m^2$ or less across the measurement area of 16,641 square microns on the at least the portion of the one or more cutting fasciae.

14. The cutting instrument of claim 13, wherein the one or more cutting fasciae have the surface roughness further comprising:
one or more of: (1) a measured maximum height ($S_t$) of 1.5 $\mu m$ or less with a standard deviation of 0.4 $\mu m$ or less within the measurement area of 16,641 square microns on the at least the portion of the one or more cutting fasciae; or (2) a measured arithmetic mean peak curvature ($S_{pc}$) of 150 $mm^{-1}$ or less with a standard deviation of 30 $mm^{-1}$ or less within the measurement area of 16,641 square microns on the at least the portion of the one or more cutting fasciae.

15. The cutting instrument of claim 13, wherein the one or more cutting fasciae have the surface roughness further comprising:
a measured maximum height ($S_t$) of 1.5 $\mu m$ or less with a standard deviation of 0.4 $\mu m$ or less within the measurement area of 16,641 square microns on the at least the portion of the one or more cutting fasciae; and
a measured arithmetic mean peak curvature ($S_{pc}$) of 150 $mm^{-1}$ or less with a standard deviation of 30 $mm^{-1}$ or less within the measurement area of 16,641 square microns on the at least the portion of the one or more cutting fasciae.

16. The cutting instrument of claim 13, wherein the surface roughness is formed into the one or more cutting fasciae using a process that removes material.

17. The cutting instrument of claim 16, wherein the process that removes the material comprises a chemical-mechanical polishing (CMP) process.

18. The cutting instrument of claim 16, wherein the process that removes the material uses a polishing pad that does not extend from one of the two opposing faces to beyond the leading edge.

19. The cutting instrument of claim 13, wherein the at least the portion of the one or more cutting fasciae comprises at least 50% of the one or more cutting fasciae.

20. The cutting instrument of claim 13, wherein:
the surface roughness is formed into the one or more cutting fasciae using a process that removes material;
the process that removes the material comprises a chemical-mechanical polishing (CMP) process;
the process that removes the material uses a polishing pad that does not extend from one of the two opposing faces to beyond the leading edge; and
the at least the portion of the one or more cutting fasciae comprises at least 50% of the one or more cutting fasciae.

* * * * *